(12) United States Patent
Asaoka et al.

(10) Patent No.: US 12,393,016 B2
(45) Date of Patent: Aug. 19, 2025

(54) ENDOSCOPE AND ENDOSCOPE SYSTEM

(71) Applicant: OLYMPUS CORPORATION, Tokyo (JP)

(72) Inventors: Nobuyoshi Asaoka, Ageo (JP); Kazuaki Tamura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 371 days.

(21) Appl. No.: 17/588,872

(22) Filed: Jan. 31, 2022

(65) Prior Publication Data

US 2022/0155580 A1   May 19, 2022

Related U.S. Application Data

(63) Continuation of application No. PCT/JP2019/031644, filed on Aug. 9, 2019.

(51) Int. Cl.
 *G02B 23/26* (2006.01)
 *F21V 8/00* (2006.01)
 *F21V 9/40* (2018.01)
(52) U.S. Cl.
 CPC ............ *G02B 23/26* (2013.01); *F21V 9/40* (2018.02); *G02B 6/0008* (2013.01)
(58) Field of Classification Search
 CPC ............ A61B 1/0661; A61B 1/00096; A61B 1/00117; G02B 6/0028; G02B 23/26; F21K 9/61; F21V 9/40; F21V 8/00
 See application file for complete search history.

(56) References Cited

U.S. PATENT DOCUMENTS

| | | | |
|---|---|---|---|
| 6,124,883 A | 9/2000 | Suzuki et al. | |
| 6,612,981 B2 | 9/2003 | Onishi et al. | |
| 6,840,901 B2 | 1/2005 | Onishi et al. | |
| 6,902,529 B2 | 6/2005 | Onishi et al. | |
| 7,522,185 B2 * | 4/2009 | Suzuki ............ | A61B 1/00165 348/70 |
| 8,849,079 B2 | 9/2014 | Yoshida et al. | |

(Continued)

FOREIGN PATENT DOCUMENTS

| | | |
|---|---|---|
| JP | S52-149133 A | 12/1977 |
| JP | H9-122065 A | 5/1997 |

(Continued)

OTHER PUBLICATIONS

International Preliminary Report on Patentability dated Feb. 17, 2022 and Written Opinion dated Oct. 21, 2019 feceived in PCT/JP2019/031644.

(Continued)

*Primary Examiner* — William J Carter
(74) *Attorney, Agent, or Firm* — Scully, Scott, Murphy & Presser, P.C.

(57) ABSTRACT

An optical apparatus having a holding portion and a tubular portion further includes a light source, a light guide which is formed of a medium having a refractive index higher than 1, and an optical converting portion. The light guide has a first light guiding area having an incidence end surface and a second light guiding area having an exit end surface. A diameter of the incidence end surface is larger than a diameter of the exit end surface, and at least a part of the second light guiding area is included in the tubular portion.

14 Claims, 20 Drawing Sheets

(56) References Cited

U.S. PATENT DOCUMENTS

| | | |
|---|---|---|
| 2001/0055061 A1 | 12/2001 | Onishi et al. |
| 2004/0082834 A1 | 4/2004 | Onishi et al. |
| 2004/0085441 A1 | 5/2004 | Onishi et al. |
| 2012/0051693 A1 | 3/2012 | Yoshida et al. |
| 2012/0053421 A1 | 3/2012 | Yoshida et al. |
| 2014/0146559 A1* | 5/2014 | Ito ................ A61B 1/0653 |
| | | 362/583 |

FOREIGN PATENT DOCUMENTS

| | | |
|---|---|---|
| JP | 2001-353124 A | 12/2001 |
| JP | 2003-126034 A | 5/2003 |
| JP | 2003-185855 A | 7/2003 |
| JP | 2011-072424 A | 4/2011 |
| JP | 2012-050504 A | 3/2012 |
| JP | 2012-050607 A | 3/2012 |
| JP | 2012-213562 A | 11/2012 |
| JP | 5172987 B2 | 3/2013 |
| WO | 2013/061590 A1 | 5/2013 |

OTHER PUBLICATIONS

Japanese Office Action dated Jun. 12, 2023, received in 2021-539705.
International Search Report dated Oct. 21, 2019 issued in PCT/JP2019/031644.
Chinese Office Action dated May 23, 2025 received in 201980099192.7.

\* cited by examiner

ENDOSCOPE AND ENDOSCOPE SYSTEM

CROSS REFERENCES

The present application is a continuation application of International Application No. PCT/JP2019/031644 filed on Aug. 9, 2019, the entire contents of which are incorporated herein by reference.

BACKGROUND OF INVENTION

Technical Field

The present disclosure relates to an endoscope and an endoscope system.

Description of the Related Art

As an optical apparatus, an endoscope has been known. An endoscope has a long and slender tubular portion. In a flexible endoscope, a flexible tubular portion is used for the tube portion. In a rigid endoscope, a rigid tubular portion is used for the tubular portion. At least a part of the tubular portion is inserted into a body or a metal tube for instance.

In an endoscope, an optical fiber is disposed at an interior of the tubular portion. Illumination light travels through the optical fiber, and is emanated from a front end of the tubular portion. When a diameter of the optical fiber is large, it is possible to make the illumination light incident efficiently on the optical fiber.

When the diameter of the optical fiber is large, a thickness of the tubular portion becomes thick. When the thickness of the tubular portion becomes thick, an insertion into a body or a metal tube cannot be carried out easily. In a case in which the tubular portion is a flexible tubular portion, it becomes difficult to bend the tuber portion.

Moreover, an image sensor and an optical system are disposed at an interior of the tubular portion. Furthermore, a through hole for putting in and taking out a treatment tool may be formed at the interior of the tubular portion. Therefore, when the diameter of the optical fiber becomes thick, a degree of freedom of a lay out is reduced.

Illuminating units in which a light guiding member is used have been disclosed in Japanese Patent Application Laid-open Publication No. 2012-050607, International Unexamined Patent Application Publication No. 2013/061590, and Japanese Patent Publication No. 5172987.

The illuminating unit disclosed in Japanese Patent Application Laid-open Publication No. 2012-050607 includes an optical fiber and a light diffusing element. The optical fiber is provided with a tapered portion. At the tapered portion, diameter becomes smaller gradually toward the light diffusing element.

The illuminating unit is disposed at a front-end portion. The front-end portion is positioned at a front end of an insertion portion. The insertion portion has the front-end portion, a bending portion, and a flexible tubular portion.

The illuminating unit disclosed in International Unexamined Patent Application Publication No. 2013/061590 includes an optical fiber, an optical filter, and a lens. A metal-plating layer is formed on an outer periphery of a front-end area of the optical fiber. At the front-end area, a diameter of the optical fiber has become small.

The illuminating unit is disposed at an endoscope front-end portion. The endoscope front-end portion is positioned at a front end of the endoscope main-body. The endoscope main-body is insertable into a body cavity, and is flexible in a portion from the endoscope front-end portion up to an endoscope base-end portion.

The illuminating unit disclosed in the Japanese Patent Publication No. 5172987 includes a plurality of LD (laser diode) chips, a light guiding member, a reflecting mirror, and a light emitting body. The plurality of LD chips is disposed in parallel. A diameter of one end of the light guiding member is larger than a diameter of the other end of thereof.

SUMMARY

An optical apparatus according to at least some embodiments of the present disclosure includes
  a holding portion,
  a tubular portion,
  a light source,
  a light guide which is formed of a medium having a refractive index higher than 1, and
  an optical converting member, wherein
  the holding portion is positioned on a light source side of the tubular portion,
  light emitted from the light source is incident on an incidence end surface of the light guide,
  light emanated from an exit end surface of the light guide is irradiated to the optical converting member,
  the light guide has a first light guiding area having the incidence end surface and a second light guiding area having an exit end surface,
  a diameter of the incidence end surface is larger than a diameter of the exit end surface, and
  at least a part of the second light guiding area is included in the tubular portion.

Moreover, a wireless endoscope according to at least some embodiments of the present disclosure includes
  an insertion portion which is long and slender, and has flexibility, and
  an operating portion which provided to a rear end of the insertion portion, wherein
  the insertion portion has a front-end portion which is provided to a front end of the insertion portion, a bending portion which provided to a rear end of the front-end portion, and flexible tube portion which is extended from a rear end of the bending portion up to a front end of the operating portion,
  a light source is disposed on an operating portion side of the rear end of the insertion portion,
  an optical converting member is disposed at the front-end portion,
  a light guide which is formed of a medium having a refractive index higher than 1 is disposed between the light source and the optical converting member,
  light emitted from the light source is incident on an incidence end surface of the light guide,
  light emanated from an exit end surface of the light guide is irradiated to the optical converting member,
  the light guide has a first light guiding area having the incidence end surface and a second light guiding area having an exit end surface,
  a diameter of the incidence end surface is larger than a diameter of the exit end surface, and
  at least a part of the second light guiding area is included in the insertion portion.

Moreover, an endoscope system according to at least some embodiments of the present disclosure includes
  The abovementioned optical apparatus or the wireless endoscope, and
  a processing apparatus.

DETAILED DESCRIPTION

Prior to the explanation of examples, action and effect of embodiments according to certain aspects of the present disclosure will be described below. In the explanation of the action and effect of the embodiments concretely, the explanation will be made by citing concrete examples. However, similar to a case of the examples to be described later, aspects exemplified thereof are only some of the aspects included in the present disclosure, and there exists a large number of variations in these aspects. Consequently, the present disclosure is not restricted to the aspects that will be exemplified.

(Optical System 1 of Present Embodiment)

An optical apparatus of the present embodiment is an optical apparatus having a holding portion and a tubular portion. The optical apparatus further includes a light source, a light guiding member which is formed of a medium having a refractive index higher than 1, and an optical converting member. The holding portion is positioned on a light-source side of the tubular portion, light emanated from the light source is incident on an incidence end surface of the light guiding member, light emanated from an exit end surface of the light guiding member is irradiated to the optical converting member. The light guiding member has a first light guiding area having the incidence end surface and a second light guiding area having an exit end surface, a diameter of the incidence end surface is larger than a diameter of the exit end surface, and at least a part of the second light guiding area is included in the tubular portion.

Diagrams used below for description include diagrams in which only the light guiding member is depicted. The light guiding member is a member which propagates light such as a light guide. For instance, it is possible to propagate light by using an optical fiber as the light guiding member. An optical fiber has a core and a clad. Since the light is propagated through the core, the core corresponds to the light guiding member. Accordingly, in each diagram, it is possible to consider that only the core is shown in the diagram.

Figure 1A:
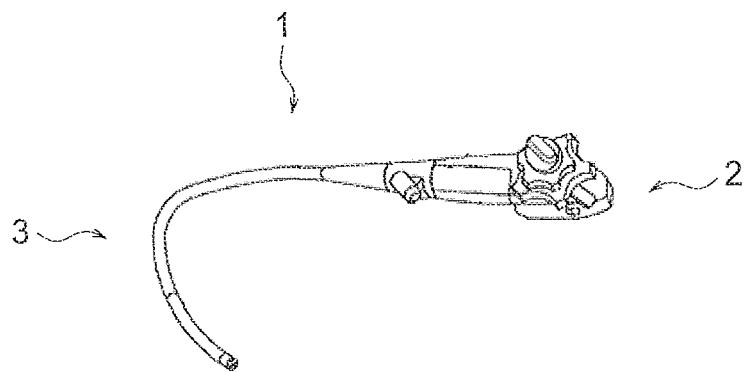
FIG. 1A and FIG. 1B are diagrams showing optical apparatuses of the present embodiment.
Figure 1B:
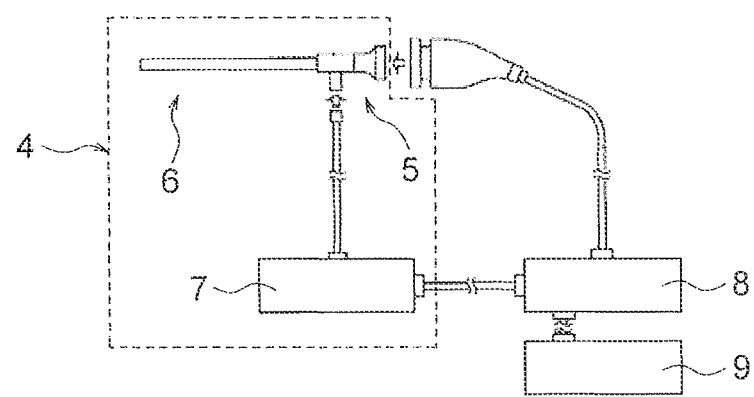

FIG. 1A and FIG. 1B are diagrams showing an optical apparatus of the present embodiment. FIG. 1A is a diagram showing an external appearance of an optical apparatus of a first example. FIG. 1B is a diagram showing an external appearance of a second example of an optical apparatus.

The optical apparatus of the first example is a flexible endoscope. As shown in FIG. 1, an optical apparatus 1 includes a holding portion 2 and a tubular portion 3. The tubular portion 3 is a flexible tubular portion. The optical apparatus 1 includes an image sensor. In the optical apparatus 1, image data acquired by the image sensor is transmitted to a processing apparatus (not shown in the diagram) by wireless transmission. Therefore, the optical apparatus 1 is a wireless endoscope.

The optical apparatus of the second example is a rigid endoscope. As shown in FIG. 1B, an optical apparatus 4 includes a holding portion 5, a tubular portion 6, and a light source unit 7. The tubular portion 6 is a rigid tubular portion. An image pickup apparatus is to be connected to the optical apparatus 4. In the optical apparatus 4, image data acquired by the image pickup apparatus is transmitted to a processing apparatus 8 by wired transmission. Accordingly, the optical apparatus 1 is a non-wireless endoscope.

In the processing apparatus 8, image processing is carried out according to the requirement. A display apparatus 9 is connected to the processing apparatus 8. An image acquired by the image sensor or an image subjected to image processing is displayed on the display apparatus 9.

Each of the optical apparatus 1 and the optical apparatus 4 includes a light source, a light guiding member, and an optical converting member. Arrangement of the light source, the light guiding member, and the optical converting member will be described below.

Figure 2A:
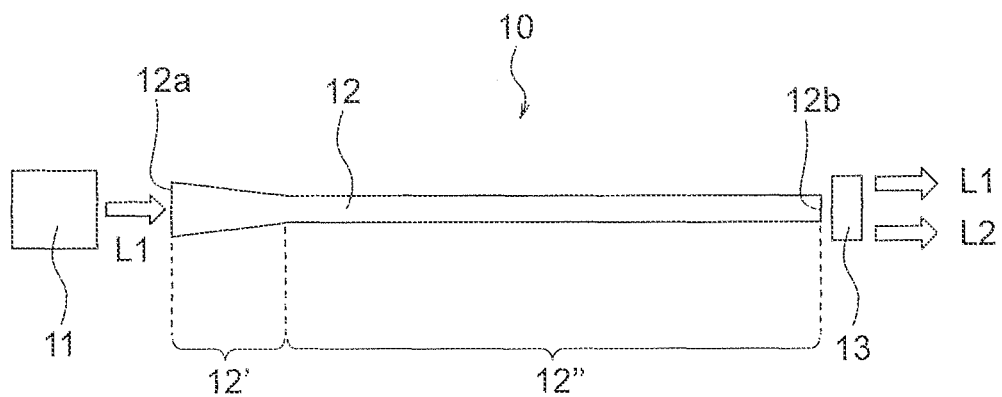
FIG. 2A and FIG. 2B are diagrams showing optical apparatuses of the present embodiment.
Figure 2B:
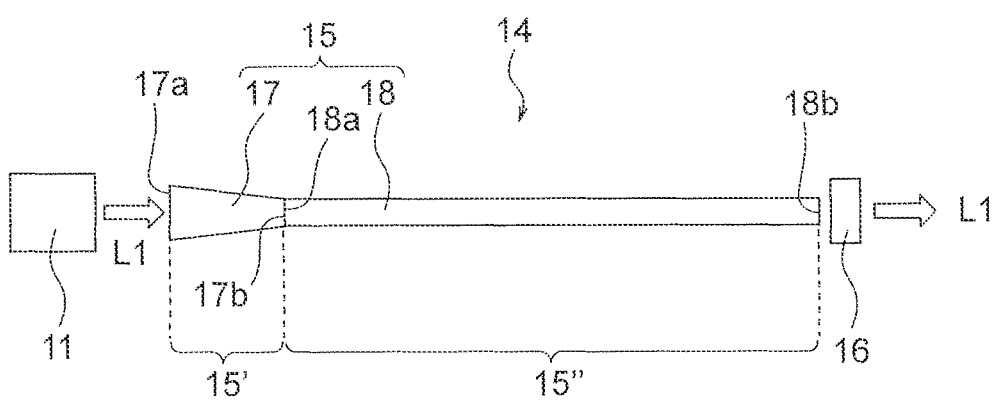

FIG. 2A and FIG. 2B are diagrams showing optical apparatuses of the present embodiment. FIG. 2A is a diagram showing a first example of an internal configuration of the optical apparatus. FIG. 2B is a diagram showing a second example of an internal configuration of the optical apparatus.

The optical converting member has a wavelength conversion effect, a light diffusion effect, or both of the wavelength conversion effect and the light diffusion effect. As the optical converting member, it is possible to use a wavelength converting member, a diffusing member, or both of the wavelength converting member and the diffusing member.

In the first example, a wavelength converting member is used as the optical converting member. In the second example, a diffusing member is used as the optical converting member.

In the first example, as shown in FIG. 2A, an optical apparatus 10 includes a light source 11, a light guiding member 12, and a wavelength converting member 13. The light guiding member 12 is formed of a medium having a refractive index higher than 1. In the light guiding member 12, a portion from an incidence end surface 12a up to an exit end surface 12b is formed of a single medium.

Light L1 of a first wavelength band is emitted from the light source 11. The light L1 of the first wavelength band reaches the light guiding member 12. It is possible to dispose a lens for example, in a space from the light source 11 up to the light guiding member 12. By disposing the lens, it is possible to make the light L1 of the first wavelength band incident efficiently on the light guiding member 12.

The light guiding member 12 has a first light guiding area 12' and a second light guiding area 12". The first light guiding area 12' has an incidence end surface 12a. The second light guiding area 12" has an exit end surface 12b.

A shape of the first light guiding area 12' is a circular truncated cone shape. The first light guiding area 12' is formed such that an apex of a circular cone is positioned on a second light guiding area 12" side. A shape of the second light guiding area 12" is a circular cylindrical shape. Without restricting to the abovementioned shapes, the shape may be a truncated pyramid shape and an angular cylindrical shape, but the aforementioned circular truncated cone shape and the circular cylindrical shape are the most preferable.

The light L1 of the first wavelength band passes through the incidence end surface 12a and is incident on the first light guiding area 12'. In the first light guiding area 12', the light L1 of the first wavelength band travels from the incidence end surface toward the second light guiding area 12".

As mentioned above, the light guiding member 12 is formed of a medium having a refractive index higher than 1. Accordingly, in the first light guiding area 12', a part of the light L1 of the first wavelength band reaches the second light guiding area 12" while repeating a total reflection at a side surface of the circular truncated cone.

In the second light guiding area 12", the light L1 of the first wavelength band travels from the first light guiding area 12' toward the exit end surface 12b.

As mentioned above, the light guiding member 12 is formed of a medium having a refractive index higher than 1. Accordingly, in the second light guiding area 12", a part of the light L1 of the first wavelength band travels toward the exit end surface 12b while repeating a total reflection at a side surface of the circular cylinder.

The light L1 of the first wavelength band that has reached the exit end surface 12b emanates from the exit end surface 12b. As a result, the light L1 of the first wavelength band is irradiated to the wavelength converting member 13.

A part of the light L1 of the first wavelength band is transmitted through the wavelength converting member 13. Light that has transmitted through the wavelength converting member 13 has not undergone wavelength conversion at the wavelength converting member 13. Accordingly, the light L1 of the first wavelength band emanates from the wavelength converting member 13.

Light remained out of the light L1 of the first wavelength band undergoes wavelength conversion at the wavelength converting member 13. In other words, at the wavelength converting member 13, light L2 of a second wavelength band is generated from the light L1 of the first wavelength band. Light having a wavelength longer than the first wavelength band is included in the light L2 of the second wavelength band.

As just described, the light L1 of the first wavelength band and the light L2 of the second wavelength emanate from the wavelength converting member 13. Accordingly, in the optical apparatus 10, it is possible to carry out illumination by using the light L1 of the first wavelength band and the light L2 of the second wavelength band.

As mentioned above, in the optical apparatus 10, the shape of the first light guiding area 12' is a circular truncated cone shape. In the circular truncated cone, an apex of the circular cone is positioned on the second light guiding area 12" side.

When the incidence end surface 12a is a bottom surface of the circular truncated cone, the bottom surface of the circular truncated cone is positioned on a light source 11 side, and an upper surface of the circular truncated cone is positioned on the second light guiding area 12" side. In the circular truncated cone, a diameter of the bottom surface is larger than a diameter of an upper surface. Accordingly, in the first light guiding area 12', a dimeter becomes smaller gradually from the incidence end surface 12a toward the second light guiding area 12".

The shape of the second light guiding area 12" is a circular cylindrical shape. Accordingly, in the second light guiding area 12", the diameter does not change.

The diameter of the upper surface of the circular truncated cone is same as a diameter of the second light guiding area 12". The diameter of the second light guiding area 12" is same as the diameter of the exit end surface 12b. As mentioned above, in the circular truncated cone, the diameter of the bottom surface is larger than the diameter of the upper surface. Accordingly, the diameter of the incidence end surface 12a is larger than the diameter of the exit end surface 12b.

In the light guiding member 12, the incidence end surface 12a is positioned on the light source 11 side. The diameter of the incidence end surface 12a is the largest diameter in the light guiding member 12. Accordingly, it is possible to make the light L1 of the first wavelength band emitted from the light source 11 incident efficiently on the incidence end surface 12a.

As mentioned above, in the light guiding member 12, the portion from the incidence end surface 12a up to the exit end surface 12b is formed of a single medium. In this case, no physical boundary is formed between the incidence end surface 12a and the exit end surface 12b. Accordingly, in the light guiding member 12, it is possible to make the light L1 of the first wavelength band that was incident on the first light guiding area 12' incident efficiently on the second light guiding area 12".

The light L1 of the first wavelength band incident on the second light guiding area 12" is irradiated to the wavelength converting member 13. In this case, since it is possible to irradiate bright light to the wavelength converting member 13, it is possible to increase brightness of light emanate from the wavelength converting member 13, or in other words, the light L2 of the second wavelength band. Accordingly, it is possible to achieve bright illumination light.

The diameter of the second light guiding area 12" is smaller than the diameter of the incidence end surface 12a. In the light guiding member 12, it is possible to make a diameter of the circular cylinder extremely small. Accordingly, it is possible to impart flexibility to the second light guiding area 12".

In the optical apparatus 10, a length of the first light guiding area 12' is shorter than a length of the second light guiding area 12". Moreover, at least a part of the second light guiding area 12" is included in the tubular portion.

As mentioned above, the diameter of the second light guiding area 12" is extremely small. By at least a part of the second light guiding area 12" being included in the tubular portion, it is possible to make a thickness of the tubular portion 3 thin in the optical apparatus 1, and to make a thickness of the tubular portion 6 thin in the optical apparatus 4.

At least a part of the tubular portion 3 is inserted into a body or a metal tube for instance. The thickness of the tubular portion 3 being thin, it is possible to insert the tubular portion 3 easily into the body or the metal tube. Moreover, in the optical apparatus 1, it is possible to bend the tubular portion 3 easily.

At least a part of the tubular portion 6 is inserted into a body or a metal tube for instance. The thickness of the tubular portion 6 being thin, it is possible to insert the tubular portion 6 easily into the body or the metal tube.

In the wavelength converting member 13, it is possible to make a surface a scattering surface. Or, it is possible to include fine particles in the wavelength converting member 13. By doing so, it is possible to diffuse the light L1 of the first wavelength band and the light L2 of the second wavelength band.

As the light guiding member 12, it is possible to use a tapered optical fiber for example. It is possible to fabricate the tapered optical fiber by stretching an optical fiber preform while superheating the optical fiber preform. In the tapered optical fiber, a radius of an incidence end surface differs from a radius of an exit end surface.

In the tapered optical fiber, an outer diameter becomes smaller from the incidence end surface toward the exit end surface. The outer diameter may become smaller gradually, or may become smaller in stages.

In the second example, an optical apparatus 14 includes the light source 11, a light guiding member 15, and a diffusing member 16. The light guiding member 15 is formed of a medium having a refractive index higher than 1. In the light guiding member 15, a portion from an incidence end surface 17a up to an exit end surface 18b is formed of two media.

The light guiding member 15 is formed by a light guiding member 17 and a light guiding member 18. The light guiding member 17 has the incidence end surface 17a and an exit end surface 17b. The light guiding member 18 has an incidence end surface 18a and the exit end surface 18b.

The light guiding member 17 and the light guiding member 18 are joined by an optical contact for example. In the optical contact, a cemented surface is formed by the exit end surface 17b and the incidence end surface 18a. It is possible to join the light guiding member 17 and the light guiding member 18 by using a cementing material.

The light guiding member 15 has a first light guiding area 15' and a second light guiding area 15". The first light guiding area 15' is formed by the light guiding member 17. The second light guiding area 15" is formed by the light guiding member 18. The first light guiding area 15' has the incidence end surface 17a. The second light guiding area 15" has the exit end surface 18b.

A shape of the light guiding member 17, in other words, a shape of the first light guiding area 15' is a circular truncated cone shape. The first light guiding area 15' is formed such that an apex of a circular cone is positioned on a second light guiding area 15" side. A shape of the light guiding member 18, or in other words, a shape of the second light guiding area 15" is a circular cylindrical shape.

Light L1 of the first wavelength band emitted from light source 11. The light L1 of the first wavelength band passes through the incidence end surface 17a and is incident on the first light guiding area 15'. In the first light guiding area 15', the light L1 of the first wavelength band travels from the incidence end surface 17a toward the exit end surface 17b.

The light guiding member 17 is formed of a medium having a refractive index higher than 1. Accordingly, in the first light guiding area 15', a part of the light L1 of the first wavelength band reaches the second light guiding area 15" while repeating a total reflection at a side surface of the circular truncated cone.

The light L1 of the first wavelength band passes through the incidence end surface 18a, and is incident on the second light guiding area 15". At the second light guiding area 15", the light L1 of the first wavelength band travels from the incidence end surface 18a toward the exit end surface 18b.

The light guiding member 18 is formed of a medium having a refractive index higher than 1. Accordingly, in the second light guiding area 15", a part of the light L1 of the first wavelength band travels toward the exit end surface 18b while repeating a total reflection at a side surface of the circular cylinder.

The light L1 of the first wavelength band that has reached the exit end surface 18b emanates from the exit end surface 18b. As a result, the light L1 of the first wavelength band is irradiated to the diffusing member 16.

The diffusing member 16 is formed of a transparent medium having a diffusing surface or is formed of a transparent medium which includes fine particles. By the diffusing surface or the fine particles, it is possible to diffuse the light L1 of the first wavelength band. Accordingly, in the optical apparatus 14, by using the diffused light L1 of the first wavelength band, it is possible to carry out illumination.

In the light guiding member 15, the incidence end surface 17a is positioned on the light source 11 side. A diameter of the incidence end surface 17a is the largest diameter in the light guiding member 15. Consequently, it is possible to make the light L1 of the first wavelength band emitted from the light source 11 incident efficiently on the incidence end surface 17a.

As mentioned above, in the light guiding member 15, the portion from the incident end surface 17a up to the exit end surface 18b is formed of two media. Consequently, a physical boundary such as, a cemented surface by an optical contact or a cemented surface by a cementing material is formed between the incidence end surface 17a and the exit end surface 18b.

However, the boundary has almost no effect on light. Accordingly, in the light guiding member 15, it is possible to make light that was incident on the first light guiding area 15' incident efficiently on the second light guiding area 15".

The light L1 of the first wavelength band incident on the second light guiding area 15" is irradiated to the diffusing member 16. In this case, since it is possible to irradiate bright light to the diffusing member 16, it is possible to increase brightness of light emanated from the diffusing member 16, or in other words, the light L1 of the first wavelength band. Accordingly, it is possible to achieve bright illumination light.

In the optical apparatus 14, a length of the first light guiding area 15' is shorter than a length of the second light guiding area 15". Moreover, at least a part of the second light guiding area 15" is included in the tubular portion.

As mentioned above, the diameter of the second light guiding area 15" is extremely small. By at least a part of the second light guiding area 15" being included in the tubular portion, it is possible to make the thickness of the tubular portion 3 thin in the optical apparatus 1, and to make the thickness of the tubular portion 6 thin in the optical apparatus 4.

In the optical apparatus 10, it is possible to dispose the diffusing member 16 adjacent to the wavelength converting member 13. In the optical apparatus 14, it is possible to dispose the wavelength converting member 13 adjacent to the diffusing member 16.

In the optical apparatus 1, the optical apparatus 4, the optical apparatus 10, and the optical apparatus 14, it is possible to irradiate light emitted from the light source to the optical converting member efficiently. Accordingly, in the abovementioned optical apparatuses, it is possible to achieve a high use efficiency of light.

In a wireless endoscope such as the optical apparatus 1, the light source is disposed inside the optical apparatus 1. Therefore, it is preferable that the optical apparatus 1 can be operated with less electric power. Particularly, it is preferable that the electric power supplied to the light source be less.

As mentioned above, in the optical apparatus 1, the use efficiency of light being high, a loss of the illumination light is less. Consequently, it is possible to make the electric power to be supplied to the light source less. As a result, it is possible to suppress a generation of heat. Moreover, even when the heat is generated, it is possible to make a heat dissipation mechanism small. Accordingly, it is possible to make the optical apparatus 1 small in size.

A preferred embodiment of the optical apparatus will be described below. As mentioned above, in the optical apparatus of the present embodiment, it is possible to use a wavelength converting member, a diffusing member, or both of a wavelength converting member and a diffusing member for the optical converting member. A case in which a wavelength converting member is used for the optical converting member will be described below.

It is possible to use the optical apparatus of the present embodiment as an illuminating apparatus or an illuminating unit.

(Optical Apparatus 2 of Present Embodiment)

In an optical apparatus of the present embodiment, it is preferable that a holding portion have an outer circumference larger than the largest outer circumference of a tubular portion, and the tubular portion have a front-end portion and a base-end portion. Moreover, it is preferable that an optical converting member be disposed at the front-end portion, the holding portion be positioned on a base-end portion side, and an entire first light guiding are be positioned on a holding-portion side of the tubular portion.

Figure 3:
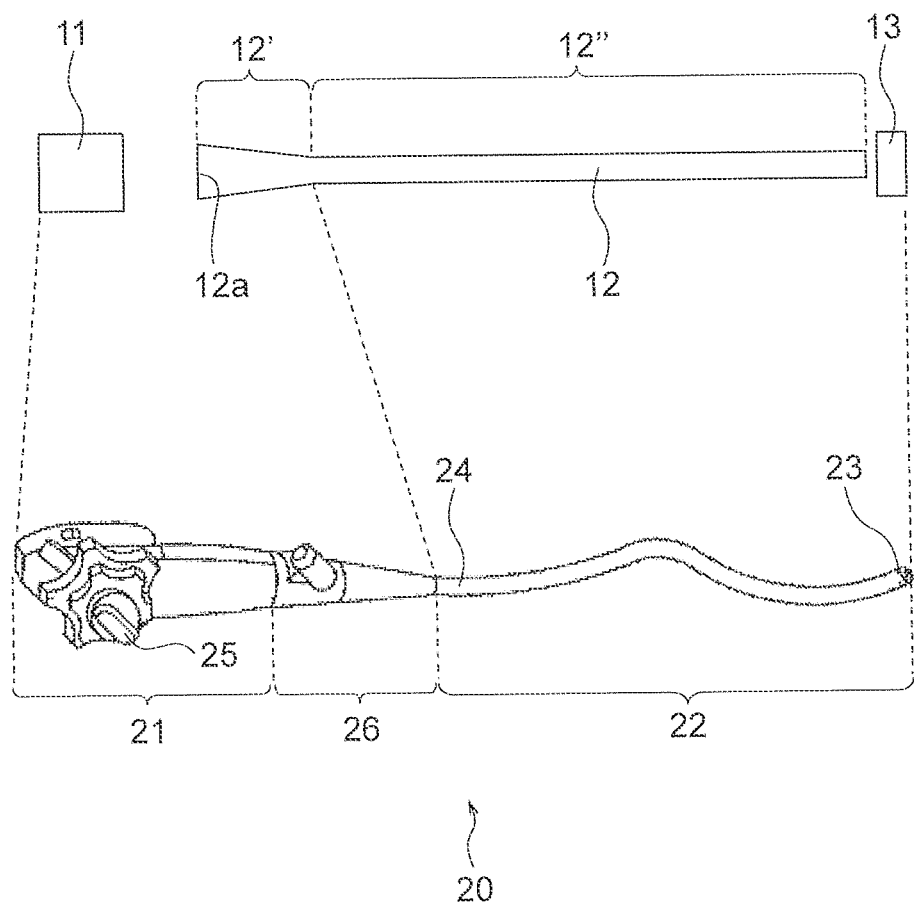
FIG. 3 is a diagram showing an optical apparatus of the present embodiment.

FIG. 3 is a diagram showing the optical apparatus of the present embodiment. Same reference numerals are assigned to components that are same as in FIG. 2A, and description thereof is omitted.

An optical apparatus 20 is a wireless endoscope. The optical apparatus 20 includes a holding portion 21 and a tubular portion 22. The tubular portion 22 is a flexible tubular portion. The holding portion 21 has an outer circumference larger than the largest outer circumference of the tubular portion 22. In the optical apparatus 20, an entire second light guiding area 12" is included in the tubular portion 22.

The tubular portion 22 has a front-end portion 23 and a base-end portion 24. The wavelength converting member 13 is positioned at the front-end portion 23. The holding portion 21 is positioned on a base-end portion 24 side. An entire first light guiding area 12' is positioned on a holding portion 21 side of the tubular portion 22.

In the optical apparatus 20, the light source 11 is disposed in the holding portion 21. The holding portion 21 has an operating portion 25. Moreover, an intermediate portion 26 is provided between the holding portion 21 and the tubular portion 22. It is possible to provide an opening for inserting a treatment tool or a bending stopper for preventing buckling of the tubular portion 22, to the intermediate portion 26.

The tubular portion 22 is mainly constituted by the second light guiding area 12". A diameter of the second light guiding area 12" is extremely small. Therefore, in the optical apparatus 20, it is possible to make a thickness of the tubular portion 22 thin. At least a part of the tubular portion 22 is inserted into a body or a metal tube. Accordingly, it is possible to insert the tubular portion 22 easily.

Moreover, the first light guiding area 12' is located between the light source 11 and the second light guiding area 12". Therefore, it is possible to make the light L1 of the first wavelength band emitted from the light source 11 incident efficiently on the first light guiding area 12'.

Furthermore, it is possible to make the light L1 of the first wavelength band travel efficiently from the first light guiding area 12' to the second light guiding area 12". In this case, since it is possible to irradiate bright light to the wavelength converting member 13, it is possible to achieve bright illumination light.

As mentioned above, the holding portion 21 has the outer circumference larger than the largest circumference of the tubular portion 22. Accordingly, by a difference in size of the outer circumference, it is possible to distinguish the holding portion 21 and the tubular portion 22.

The first light guiding area 12' is located on a holding portion 21 side of the tubular portion 22. Consequently, a space enough to position the first light guiding area 12' is secured on the holding portion 21 side of the tubular portion 22. An outer circumference of the holding portion 21 is to be set to include the space for positioning the first light guiding area 12'.

Or, an arrangement may be made such that when the incidence end surface 12a, a cross-sectional surface of the tubular portion 22, and a cross-sectional surface of the holding portion 21 are overlapped, the incidence end surface 12a is included in the cross-sectional surface of the holding portion 21.

Figure 4:
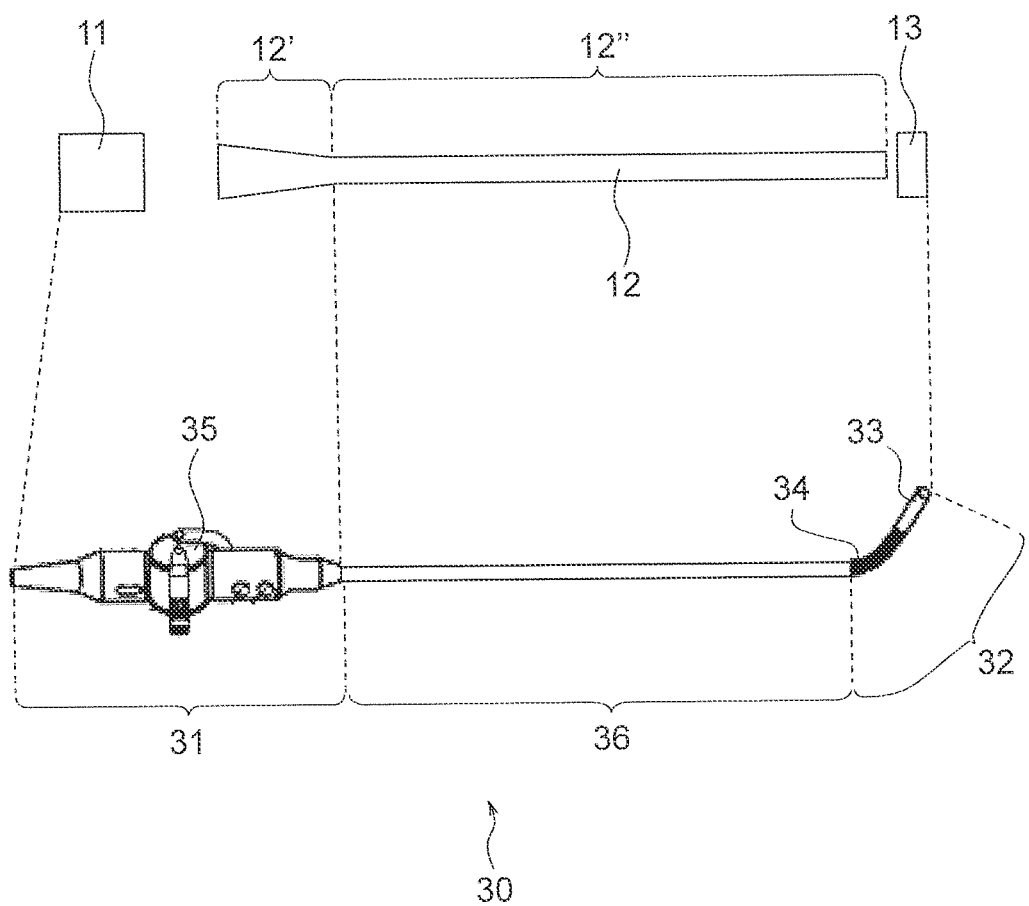
FIG. 4 is a diagram showing an optical apparatus of the present embodiment.

FIG. 4 is a diagram showing an optical apparatus of the present embodiment. Same reference numerals are assigned to components that are same as in FIG. 2A, and description thereof is omitted.

An optical apparatus 30 is a wireless endoscope. The optical apparatus 30 includes a holding portion 31 and a tubular portion 32. The tubular portion 32 is a flexible tubular portion. The holding portion 31 has an outer circumference larger than the largest outer circumference of the tubular portion 32. In the optical apparatus 30, a part of the second light guiding area 12" is included in the tubular portion 32.

The tubular portion 32 has a front-end portion 33 and a base-end portion 34. The wavelength converting member 13 is positioned at the front-end portion 33. The holding portion 31 is positioned on a base-end portion 34 side. The entire first light guiding area 12' is located on a holding portion 31 side of the tubular portion 32.

In the optical apparatus 30, the light source 11 is disposed in the holding portion 31. The holding portion 31 has an operating portion 35. Moreover, an intermediate portion 36 is provided between the holding portion 31 and the tubular portion 32. In the optical apparatus 30, the second light guiding area 12" is included even in the intermediate portion 36.

The tubular portion 32 is mainly constituted by the second light guiding area 12". The diameter of the second light guiding area 12" is extremely small. Therefore, in the optical apparatus 30, it is possible to make a thickness of the tubular portion 22 thin. At least a part of the tubular portion 22 is inserted into a body or a metal tube. Accordingly, it is possible to insert the tubular portion 32 easily.

Moreover, the first light guiding area 12' is located between the light source 11 and the second light guiding area 12". Therefore, it is possible to make the light L1 of the first wavelength band emitted from the light source 11 incident efficiently on the first light guiding area 12'.

Furthermore, it is possible to make the light L1 of the first wavelength band travel efficiently from the first light guiding area 12' to the second light guiding area 12". In this case, since it is possible to irradiate bright light to the wavelength converting member 13, it is possible to achieve bright illumination light.

Moreover, even the intermediate portion 36 is mainly constituted by the second light guiding area 12". Accordingly, it is possible to make a thickness of the intermediate portion 36 same as a thickness of the tubular portion 32. In other words, it is possible to make the thickness of the intermediate portion 36 thin. As a result, it is possible to insert at least a part of the intermediate portion 36 into a body or a metal tube.

It is possible to make the intermediate portion 36 a rigid tubular portion. In a case in which a length of the intermediate portion 36 is extremely large as compared to a length of the tubular portion 32, the optical apparatus 30 can be deemed as a rigid endoscope. In a case in which, the length of the intermediate portion 36 is extremely short as compared to the length of the tubular portion 32, the optical apparatus 30 can be deemed as a flexible endoscope.

Figure 5:
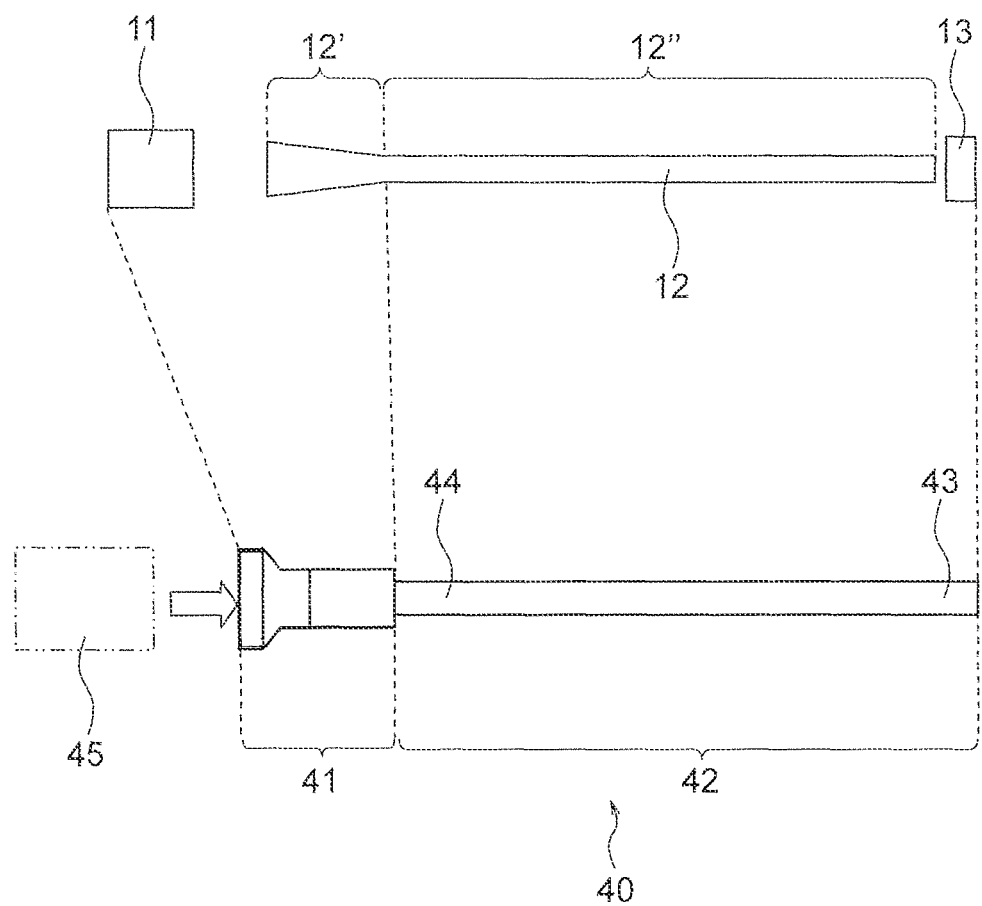
FIG. 5 is a diagram showing an optical apparatus of the present embodiment.

FIG. 5 is a diagram showing an optical apparatus of the present embodiment. Same reference numerals are assigned to components that are same as in FIG. 2A, and description thereof is omitted.

An optical apparatus 40 is a wireless endoscope. The optical apparatus 40 includes a holding portion 41 and a tubular portion 42. The tubular portion 42 is a rigid tubular portion. The holding portion 41 has an outer circumference larger than the largest outer circumference of the tubular portion 42. In the optical apparatus 40, the entire second light guiding area 12" is included in the tubular portion 42.

The tubular portion 42 has a front-end portion 43 and a base-end portion 44. The wavelength converting member 13 is positioned at the front-end portion 43. The holding portion 41 is located on a base-end portion 44 side. The entire first light guiding area 12' is located on a holding portion 41 side of the tubular portion 42.

In the optical apparatus 40, the light source 11 is disposed in the holding portion 41. The holding portion 41 has a connecting portion. It is possible to mount an image pickup apparatus 45 on the holding portion 41 via the connecting portion. The image pickup apparatus 45 has an image sensor. In the image pickup apparatus 45, acquired image data is transmitted to a processing apparatus by wireless transmission. A wired image pickup apparatus may be used as the image pickup apparatus 45. In this case, the optical apparatus 40 becomes a non-wireless endoscope.

In the optical apparatus 40, the holding portion 41 and the tubular portion 42 are connected directly. However, an intermediate portion may be provided between the holding portion 41 and the tubular portion 42, or, a part of the holding portion 41 may be made the intermediate portion. It is possible to provide an opening for inserting a treatment tool, to the intermediate portion.

The tubular portion 42 is mainly constituted by the second light guiding area 12". The diameter of the second light guiding area 12" is extremely small. Therefore, in the optical apparatus 40, it is possible to make a thickness of the tubular portion 42 thin. At least a part of the tubular portion 42 is inserted into a body or a metal tube. Accordingly, it is possible to insert the tubular portion 42 easily.

Moreover, the first light guiding area 12' is located between the light source 11 and the second light guiding area 12". Therefore, it is possible to make the light L1 of the first wavelength band emitted from the light source 11 incident efficiently on the first light guiding area 12'.

Furthermore, it is possible to make the light L1 of the first wavelength band travel efficiently from the first light guiding area 12' to the second light guiding area 12". In this case, since it is possible to irradiate bright light to the wavelength converting member 13, it is possible to achieve bright illumination light.

(Optical Apparatus 3 of Present Embodiment)

In an optical apparatus of the present embodiment, it is preferable that a holding portion have an outer circumference larger than the largest outer circumference of a tubular portion, the entire second light guiding area be included in the tubular portion, and the tubular portion have a front-end portion and a base-end portion. Moreover, it is preferable that an optical converting member be disposed at the front-end portion, the holding portion be positioned on a base-end portion side, and at least a part of the first light guiding area be included in the tubular portion.

Figure 6:
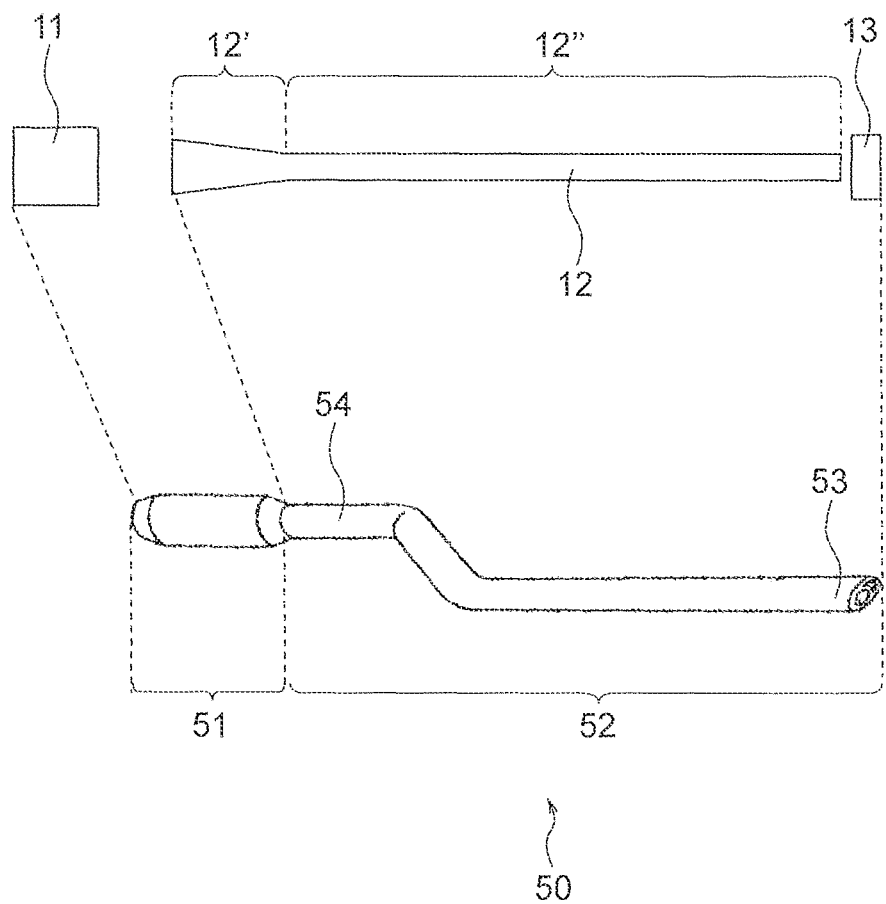
FIG. 6 is a diagram showing an optical apparatus of the present embodiment.

FIG. 6 is a diagram showing the optical apparatus of the present embodiment. Same reference numerals are assigned to components that are same as in FIG. 2A, and description thereof is omitted.

An optical apparatus 50 is a wireless endoscope. The optical apparatus 50 includes a holding portion 51 and a tubular portion 52. The tubular portion 52 is a rigid tubular portion. The holding portion 51 has an outer circumference larger than the largest outer circumference of the tubular portion 52. In the optical apparatus 50, the entire second light guiding area 12" is included in the tubular portion 52.

The tubular portion 52 has a front-end portion 53 and a base-end portion 54. The wavelength converting member 13 is positioned at the front-end portion 53. The holding portion 51 is positioned on a base-end portion 54 side. The entire first light guiding area 12' is included in the tubular portion 52.

In the optical apparatus 50, the light source 11 is disposed in the holding portion 51. The holding portion 51 and the tubular portion 52 are connected directly. However, an intermediate portion may be provided between the holding portion 51 and the tubular portion 52, or a part of the holding portion 51 may be made the intermediate portion. It is possible to provide an opening for inserting a treatment tool, to the intermediate portion.

At least a part of the tubular portion 52 is inserted into a body or a metal tube for instance. As mentioned above, in the optical apparatus 50, the entire first light guiding area 12' and the entire light guiding area 12" are included in the tubular portion 52. Therefore, comparing with the optical apparatus 40, a thickness of the tubular part 52 becomes somewhat thick.

However, in a metal tube having a large diameter, it is possible to insert the tubular portion 52 without a hitch.

Moreover, as compared to a case in which the entire first light guiding area 12' is positioned in the holding portion 51, it is possible to make a length of the holding portion 51 short.

Moreover, the first light guiding area 12' is located between the light source 11 and the second light guiding area 12". Therefore, it is possible to make the light L1 of the first wavelength band emitted from the light source 11 incident efficiently on the first light guiding area 12'.

Furthermore, it is possible to make the light L1 of the first wavelength band travel efficiently from the first light guiding area 12' to the second light guiding area 12". In this case, since it is possible to irradiate bright light to the wavelength converting member 13, it is possible to achieve bright illumination light.

Figure 7:
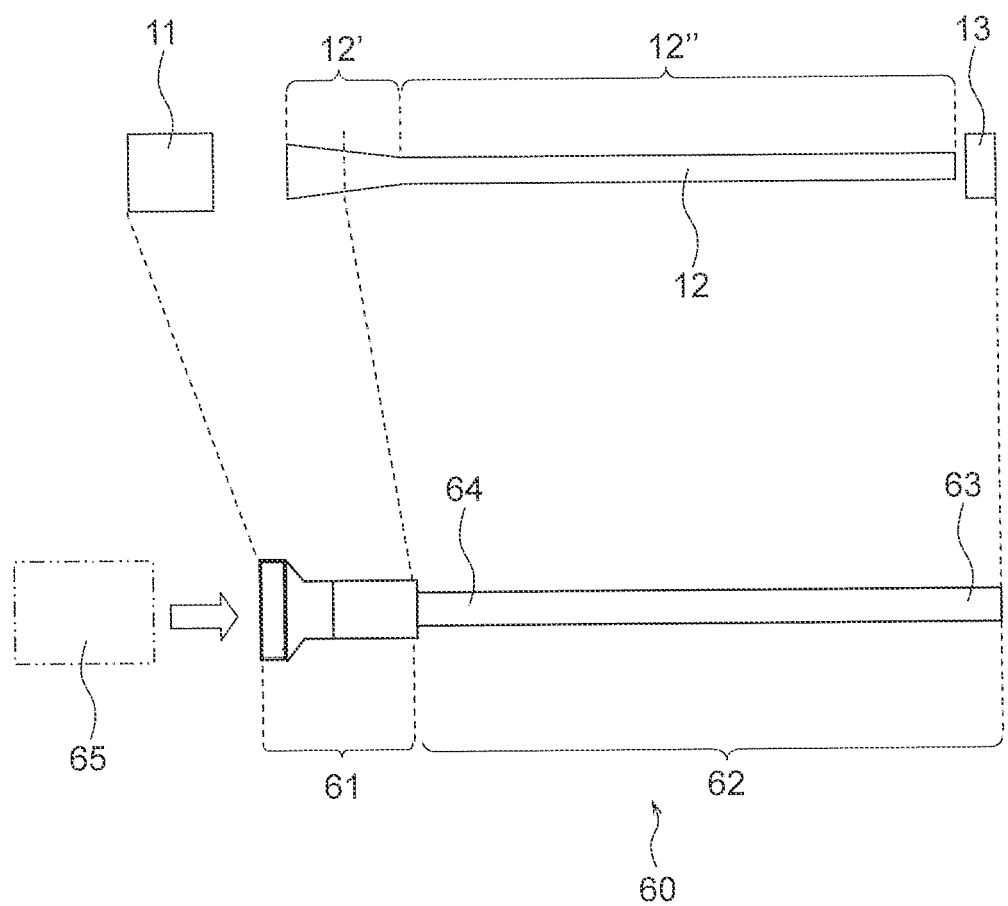
FIG. 7 is a diagram showing an optical apparatus of the present embodiment.

FIG. 7 is a diagram showing an optical apparatus of the present embodiment. Same reference numerals are assigned to components that are same as in FIG. 2A, and description thereof is omitted.

An optical apparatus 60 is a wireless endoscope. The optical apparatus 60 includes a holding portion 61 and a tubular portion 62. The tubular portion 62 is a rigid tubular portion. The holding portion 61 has an outer circumference larger than the largest outer circumference of the tubular portion 62. In the optical apparatus 60, the entire second light guiding area 12" is included in the tubular portion 62.

The tubular portion 62 has a front-end portion 63 and a base-end portion 64. The wavelength converting member 13 is positioned at the front-end portion 63. The holding portion 61 is positioned on a base-end portion 64 side. A part of the first light guiding area 12' is included in the tubular portion 62.

In the optical apparatus 60, the light source 11 is disposed in the holding portion 61. The holding portion 61 and the tubular portion 62 are connected directly. However, an intermediate portion may be provided between the holding portion 61 and the tubular portion 62, or a part of the holding portion 61 may be made the intermediate portion. It is possible to provide an opening for inserting a treatment tool, to the intermediate portion.

At least a part of the tubular portion 62 is inserted into a body or a metal tube for instance. As mentioned above, in the optical apparatus 60, at least a part of the first light guiding area 12' and the entire second light guiding area 12" are included in the tubular portion 62. Therefore, comparing with the optical apparatus 40 for instance, a thickness of the tubular portion 62 is somewhat thick.

However, in a metal tube having a large diameter, it is possible to insert the tubular portion 62 without a hitch. Moreover, as compared to a case in which the entire first light guiding area 12' is positioned in the holding portion 61, it is possible to make a length of the holding portion 61 short.

Moreover, the first light guiding area 12' is located between the light source 11 and the second light guiding area 12". Therefore, it is possible to make the light L1 of the first wavelength band emitted from the light source 11 incident efficiently on the first light guiding area 12'.

Furthermore, it is possible to make the light L1 of the first wavelength band travel efficiently from the first light guiding area 12' to the second light guiding area 12". In this case, since it is possible to irradiate bright light to the wavelength converting member 13, it is possible to achieve bright illumination light.

(Optical Apparatus 4 of Present Embodiment)

In an optical apparatus of the present embodiment, it is preferable that a tubular portion be formed by a first tubular portion and a second tubular portion, the first tubular portion have a first front-end portion and a first base-end portion, and the second tubular portion have a second front-end portion and a second base-end portion. Moreover, it is preferable that an optical converting member be disposed in the first front-end portion, a holding portion be positioned between the first base-end portion and the second front-end portion, a connecting portion be positioned on a second base-end portion side, the entire second light guiding area be included in the tubular portion, and the first light guiding area be positioned on a connecting-portion side of the second tubular portion.

Figure 8:
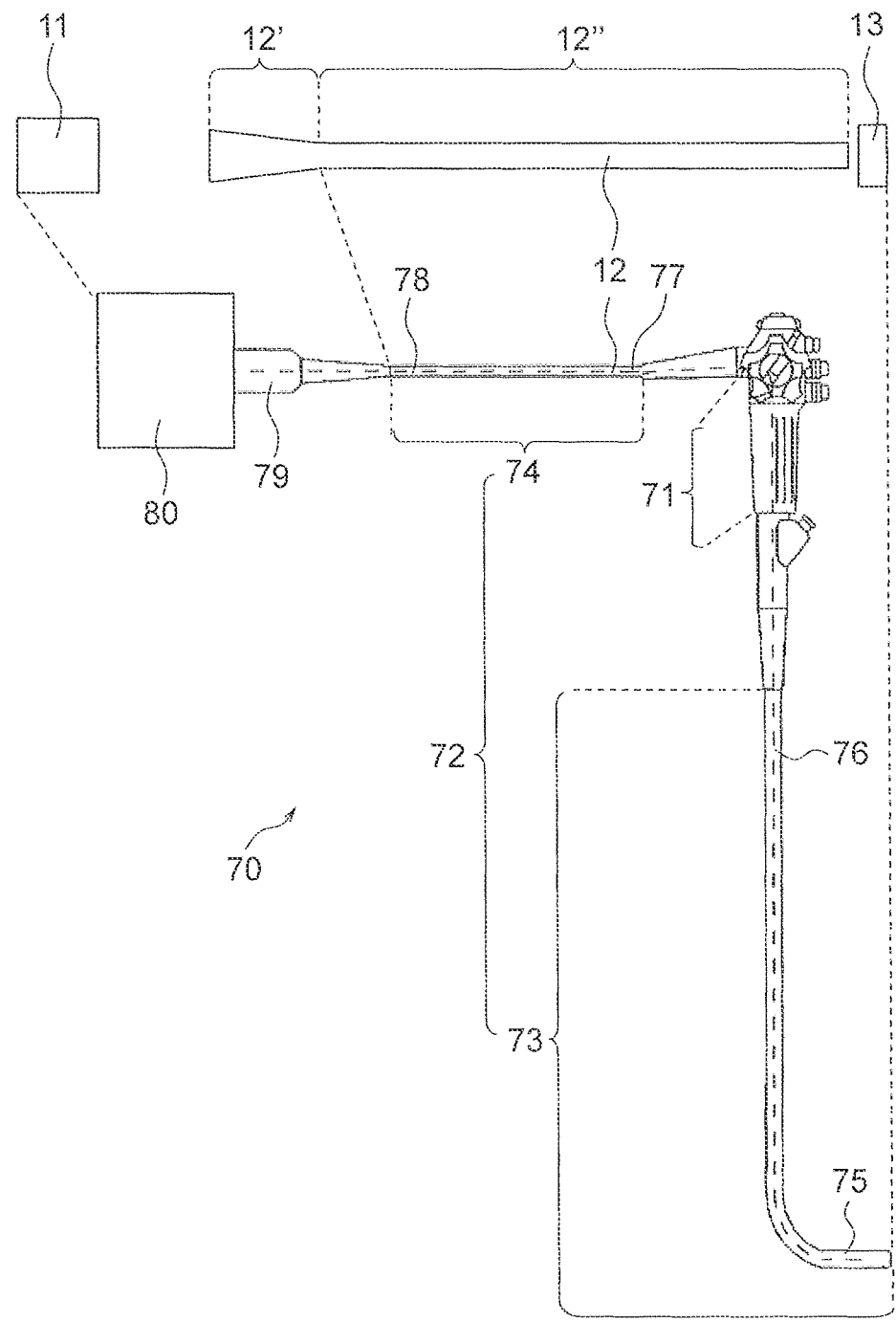
FIG. 8 is a diagram showing an optical apparatus of the present embodiment.

FIG. 8 is a diagram showing the optical apparatus of the present embodiment. Same reference numerals are assigned to components that are same as in FIG. 2A, and description thereof is omitted.

An optical apparatus 70 is a non-wireless endoscope. The optical apparatus 70 includes a holding portion 71 and a tubular portion 72. The tubular portion 72 is a flexible tubular portion. The tubular portion 72 is formed by a first tubular portion 73 and a second tubular portion 74.

The first tubular portion 73 has a first front-end portion 75 and a first base-end portion 76. The second tubular portion 74 has a second front-end portion 77 and a second base-end portion 78.

The wavelength converting member 13 is positioned in the first front-end portion 75. The holding portion 71 is positioned between the first base-end portion 76 and the second front-end portion 77. A connecting portion 79 is positioned on a second base-end portion 78 side.

A light source unit 80 is connected to the connecting portion 79. The light source 11 is disposed in the light source unit 80.

In the optical apparatus 70, the entire second light guiding area 12" is included in the tubular portion 72. The first light guiding area 12' is positioned on a connecting portion 79 side of the second tubular portion 74. The first light guiding area 12' may be positioned in the connecting portion 79 or may be positioned in the light source unit 80.

The first tubular portion 73 is mainly constituted by the second light guiding area 12". The diameter of the second light guiding area 12" is extremely small. Therefore, in the optical apparatus 70, it is possible to make a thickness of the first tubular portion 73 thin. At least a part of the first tubular portion 73 is inserted into a body or a metal tube. Accordingly, it is possible to insert the first tubular portion 73 easily.

Moreover, the first light guiding area 12' is located between the light source 11 and the second light guiding area 12". Therefore, it is possible to make the light L1 of the first wavelength band emitted from the light source 11 incident efficiently on the first light guiding area 12'.

Furthermore, it is possible to make the light L1 of the first wavelength band travel efficiently from the first light guiding area 12' to the second light guiding area 12". In this case, since it is possible to irradiate bright light to the wavelength converting member 13, it is possible to achieve bright illumination light.

Moreover, the second tubular portion 74 is mainly constituted by the second light guiding area 12". The diameter of the second light guiding area 12" is extremely small. Therefore, it is possible to make a thickness of the second tubular portion 74 thin. As a result, handling of the optical apparatus 70 becomes easy.

(Front-End Portion of Optical Apparatus)

As mentioned above, in the optical apparatus of the present embodiment, it is possible to achieve bright illumination light. The reason being that, it is possible to make light emitted from the light source incident efficiently on the light guiding member and it is possible to make the light that is incident travel efficiently. Furthermore, it is possible to achieve bright illumination light for to the following reasons.

In the description below, light having a peak wavelength of 415 nm will be referred to as 'excitation light $L_{415}$', light having a peak wavelength of 450 nm will be referred to as 'excitation light $L_{450}$', light having a peak wavelength of 540 nm will be referred to as 'radiation light $L_{540}$', and light having a peak wavelength of 575 nm will be referred to as 'radiation light $L_{575}$'.

In the optical apparatus of the present embodiment, an optical converting unit is disposed in the front-end portion of the tubular portion. The optical converting unit includes a wavelength converting member. In this case, the optical converting unit functions as the wavelength converting unit.

Figure 9A:
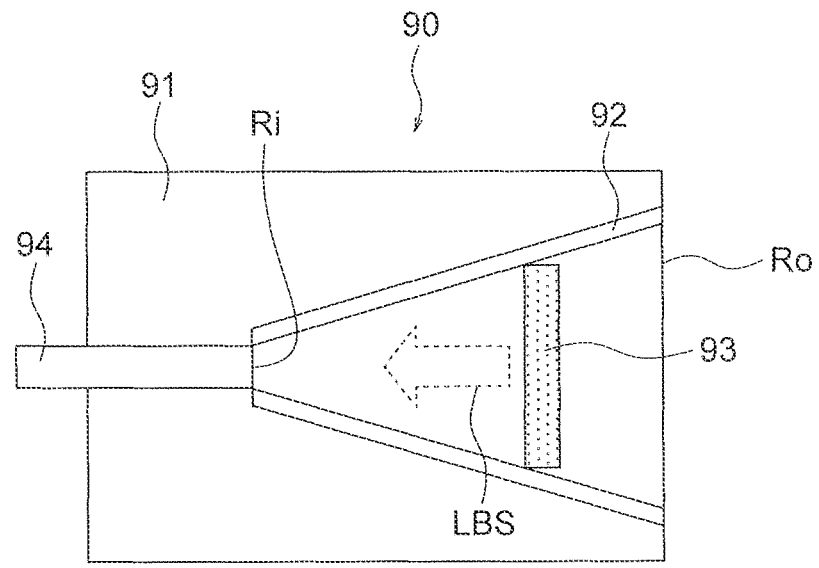
FIG. 9A and FIG. 9B are diagrams showing a first example of a wavelength converting unit.
Figure 9B:
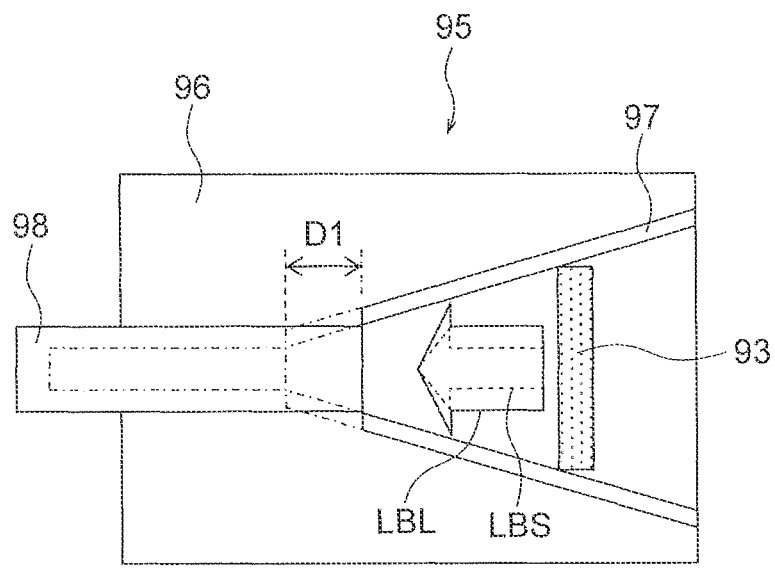

FIG. 9A and FIG. 9B are diagrams showing a first example of the wavelength converting unit. FIG. 9A is a diagram showing a case in which the diameter of the second light guiding area 12" is small. FIG. 9B is a diagram showing a case in which the area of the second light guiding area 12" is large.

As shown in FIG. 9A, a wavelength converting unit 90 includes a holding member 91, a reflecting member 92, and a wavelength converting member 93. Moreover, as shown in FIG. 9B, a wavelength converting unit 95 includes a holding member 96, a reflecting member 97, and a wavelength converting member 93.

A structure of the wavelength converting unit 95 is nearly same as a structure of the wavelength converting unit 90. Therefore, description of the structure of the wavelength converting unit 95 will be omitted.

In the wavelength converting unit 90, a recess is formed on one end of the holding member 91. The reflecting member 92 is disposed in the recess. By the reflecting member 92, a reflecting surface is formed on an inner peripheral surface of the recess.

The reflecting member 92 is a hollow member. The wavelength converting member 93 is disposed in a hollow portion. It is possible to fill the hollow portion with a transparent medium for example. Accordingly, it is possible to hold the wavelength converting member 93.

At the other end of the holding member 91, a through hole is formed toward the recess. A light guiding member 94 is inserted into the through hole. In the wavelength converting unit 95, a light guiding member 98 is inserted into the through hole.

A shape of the recess being a circular truncated cone shape, the reflecting member 92 has a shape same as a side surface of the circular truncated cone. In the recess, a diameter of the one end is smaller than a diameter of the other end. Therefore, in the reflecting member 92, the diameter of the one end (hereinafter, referred to as 'incidence end surface Ri') is smaller than the diameter of the other end (hereinafter, referred to as 'exit end surface Ro').

The incidence end surface Ri is positioned on a through hole side. A diameter of the incidence end surface Ri is same as a diameter of the through hole, or in other words, a diameter of the second light guiding area of the light guiding member 94.

As shown in FIG. 2A, the light L1 of the first wavelength band is emitted from the light source 11. The light L1 of the first wavelength band emanates from the light guiding member 12. In FIG. 9A, the light L1 of the first wavelength band emanates from the light guiding member 94. The light L1 of the first wavelength band is irradiated to the wavelength converting member 93. A fluorescent substance is used for the wavelength converting member 93. In the fluorescent substance, light of a wavelength longer than a wavelength of irradiated light, or in other words, light L2 of a second wavelength band, is generated.

As the fluorescent substance, YAG:Ce (Yttrium Aluminum Garnet doped with cerium) fluorescent substance (hereinafter, referred to as 'YAG fluorescent substance') can be used. The YAG fluorescent substance has a composition indicated by $Y_3A_{15}O_{12}$. When the excitation light $L_{450}$ is irradiated as the light L1 of the first wavelength band to the YAG fluorescent substance, the radiation light $L_{575}$ is generated from the YAG fluorescent substance as the light L2 of the second wavelength band.

However, a part of the irradiated light passes through the YAG fluorescent substance. Accordingly, the excitation light $L_{450}$ and the radiation light $L_{575}$ emanate from the wavelength converting member 93. The excitation light $L_{450}$ is light of blue color and the radiation light $L_{575}$ is light of yellow color. Accordingly, light close to nearly white color emanates from the exit end surface Ro.

A part of the excitation light $L_{450}$ irradiated to the wavelength converting member 93 is reflected at the wavelength converting member 93. In the wavelength converting unit 90, a part of the excitation light $L_{450}$ that was reflected travels toward the light guiding member 94. In the wavelength converting unit 95, a part of the excitation light $L_{450}$ that was reflected travels toward the light guiding member 98.

The radiation light $L_{575}$ is fluorescent light. The fluorescent light travels in all directions. Therefore, in the wavelength converting unit 90, a part of the radiation light $L_{575}$ travels toward the light guiding member 94. In the wavelength converting unit 95, a part of the radiation light $L_{575}$ travels toward the light guiding member 98.

In FIG. 9A, the excitation light $L_{450}$ and the radiation light $L_{575}$ (hereinafter, referred to as 'light beam LBS') incident on the light guiding member 94 are indicated by a dash-line arrow. In FIG. 9B, the excitation light $L_{450}$ and the radiation light $L_{575}$ (hereinafter, referred to as 'light beam LBL') incident on the light guiding member 98 are indicated by a solid-line arrow.

The light beam LBS being incident on the light guiding member 94, the light beam LBS does not emanate from the exit end surface Ro. Moreover, the light beam LBL being incident on the light guiding member 98, the light beam LBL does not emanate from the exit end surface Ro. Therefore, it is not possible to use both the light beam LBS and the light beam LBL as illumination light. A size of the arrow indicates a size of the light beam which is not used as the illumination light.

As mentioned above, the diameter of the second light guiding area of the light guiding member 94 is smaller than the diameter of the second light guiding area of the light guiding member 98. Therefore, a size of the dash-line arrow is smaller than a size of the solid-line arrow. In other words, a size of the light beam LBS is smaller than a size of the light beam LBL. Therefore, in the wavelength converting unit 90, it is possible to reduce the light incident on the light guiding member as compared to that in the wavelength converting unit 95. As a result, in the wavelength converting unit 90, it is possible to reduce a loss of the illumination light as compared to that in the wavelength converting unit 95.

It is possible to impart a diffusion effect to the wavelength converting member 93. For instance, by providing a diffusing surface to or by including fine particles in the wavelength converting member 93, it is possible to achieve the diffusion effect. In a case in which the wavelength converting member 93 has the diffusion effect, scattered light of the excitation light $L_{450}$ and scattered light of the radiation light $L_{575}$ (hereinafter, referred to as 'scattered light $L_{BY}$') are generated.

The scattered light $L_{BY}$ travels in all directions. Therefore, in the wavelength converting unit 90, a part of the scattered light $L_{BY}$ travels toward the light guiding member 94. Even in the wavelength converting unit 95, a part of the scattered light $L_{BY}$ travels toward the light guiding member 98. Therefore, a part of the scattered light $L_{BY}$ is included in each of the light beam LBS and the light beam LBL.

It is possible to use a diffusing member instead of the wavelength converting member 93. In this case, the wavelength converting unit functions as a light diffusing unit. Although no fluorescent light is generated by the diffusing member, scattered light is generated. The scattered light travels in all directions. Therefore, in the wavelength converting unit 90, a part of the scattered light travels toward the light guiding member 94. Even in the wavelength converting unit 95, a part of the scattered light travels toward the light guiding member 98. Therefore, when the diffusing member is used, a part of the scattered light is included in each of the light beam LBS and the light beam LBL.

As mentioned above, the size of the light beam LBS is smaller than the size of the light beam LBL. Therefore, in the wavelength converting unit 90, it is possible to reduce the light incident on the light guiding member as compared to that in the wavelength converting unit 95. As a result, in the wavelength converting unit 90, it is possible to reduce a loss of the illumination light as compared to that in the wavelength converting unit 95.

Moreover, a reflecting surface is formed on an inner peripheral surface of the recess. The larger the area of the reflecting surface, the larger is the proportion of the light L1 of the first wavelength band and the proportion of the light L2 of the second wavelength band travelling toward the exit end surface Ro. As shown in FIG. 9B, a reflecting surface does not exist in a range D1 in the wavelength converting unit 95, whereas, a reflecting surface does exist at a location corresponding to the range D1 in the wavelength converting unit 90. Therefore, in the wavelength converting unit 90, it is possible to make large the proportion of directing the light L2 of the second wavelength band toward the exit end surface Ro, as compared to that in the wavelength converting unit 95.

In the optical apparatus of the present embodiment, the first light guiding area is disposed on a holding portion side of the second light guiding area. Therefore, it is possible to make the diameter of the second light guiding area extremely small. In this case, it is possible to reduce the proportion of the light L2 of the second wavelength band incident on the second light guiding area, and moreover, it is possible to make large the proportion of directing the light L2 of the second wavelength band toward the exit end surface Ro. As a result, in the optical apparatus of the present embodiment, it is possible to achieve bright illumination light.

Figure 10A:
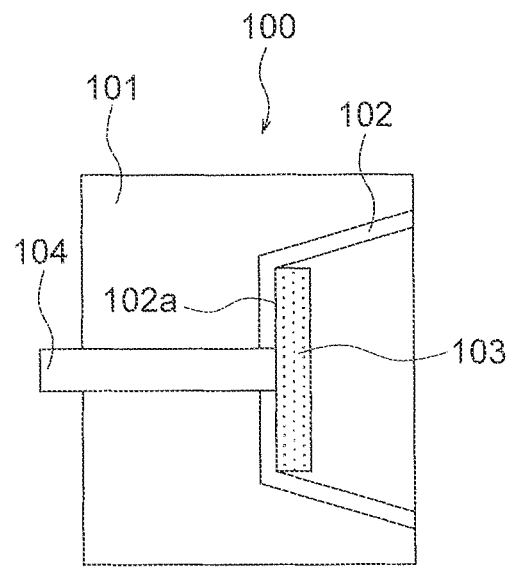
FIG. 10A and FIG. 10B are diagrams showing a second example of a wavelength converting unit.
Figure 10B:
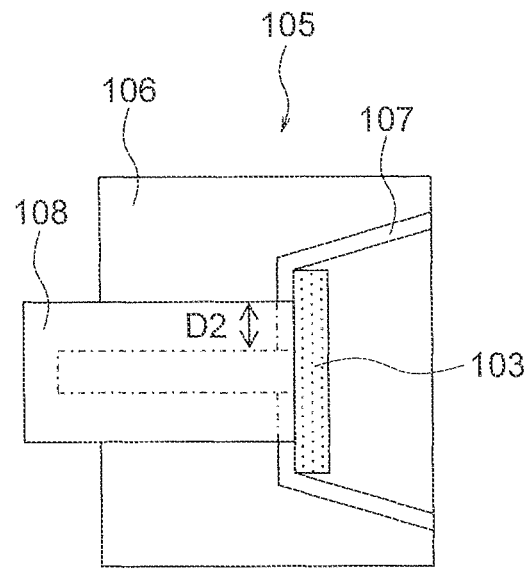

FIG. 10A and FIG. 10B are diagrams showing a second example of the wavelength converting unit. FIG. 10A is diagram showing a case in which the diameter of the second light guiding area 12" is small. FIG. 10B is a diagram showing a case in which the diameter of the second light guiding area 12" is large.

As shown in FIG. 10A, a wavelength converting unit 100 includes a holding member 101, a reflecting member 102, and a wavelength converting member 103. Moreover, as shown in FIG. 10B, a wavelength converting unit 105 includes a holding member 106, a reflecting member 107, and a wavelength converting member 103.

A structure of the wavelength converting unit 105 is nearly same as a structure of the wavelength converting unit 100. Therefore, description of the structure of the wavelength converting unit 105 will be omitted.

In the wavelength converting unit 100, a recess is formed on one end of the holding member 101. The reflecting member 102 is disposed in the recess. By the reflecting member 102, a reflecting surface is formed on an inner peripheral surface of the recess.

The reflecting member 102 is a hollow member. The wavelength converting member 103 is disposed in a hollow portion. It is possible to fill the hollow portion with a transparent medium for example. Accordingly, it is possible to hold the wavelength converting member 103.

At the other end of the holding member 101, a through hole is formed toward the recess. A light guiding member 104 is inserted into the through hole. In the wavelength converting unit 105, a light guiding member 108 is inserted into the through hole.

A shape of the recess being a circular truncated cone shape, the reflecting member 102 has a shape same as a side surface of the circular truncated cone. In the recess, a diameter of the one end is smaller than a diameter of the other end. Therefore, in the reflecting member 102, a diameter of an incidence end surface Ri is smaller than a diameter of an exit end surface Ro.

The incidence end surface Ri is positioned on a through hole side. The diameter of the incidence end surface Ri is larger than a diameter of the through hole, or in other words, a diameter of the second light guiding area of the light guiding member 104. Therefore, a reflecting surface 102a having an annular shape is formed on the incidence end surface Ri of the reflecting member 102. The light guiding member 104 is positioned at an inner edge side of the reflecting surface 102a.

In FIG. 10A, light L1 of the first wavelength band emanates from the light guiding member 104. The light L1 of the first wavelength band is irradiated to the wavelength converting member 103. A fluorescent substance is used for the wavelength converting member 103. In the fluorescent substance, light of a wavelength longer than a wavelength of the irradiated light, or in other words, light L2 of a second wavelength band, is generated.

As the fluorescent substance, Europium-activated sialon phosphor (hereinafter, referred to as 'sialon phosphor') can be used. When the excitation light $L_{415}$ is irradiated as the light L1 of the first wavelength band to the sialon phosphor, the radiation light $L_{540}$ is generated from the sialon phosphor as the light L2 of the second wavelength band.

However, a part of the irradiated light passes through the sialon phosphor. Accordingly, the excitation light $L_{415}$ and the radiation light $L_{540}$ emanate from the wavelength converting member 103. The excitation light $L_{415}$ is light of bluish-violet color and the radiation light $L_{540}$ is light of green color. Accordingly, light close to nearly bluish-green color emanates from the exit end surface Ro.

A part of the excitation light $L_{415}$ irradiated to the wavelength converting member 103 is reflected at the wavelength converting member 103. In the wavelength converting unit 100, a part of the excitation light $L_{415}$ that was reflected travels toward the light guiding member 104. In the wavelength converting unit 105, a part of the excitation light $L_{415}$ that was reflected travels toward the light guiding member 108.

The radiation light $L_{540}$ is fluorescent light. The fluorescent light travels in all directions. Therefore, in the wavelength converting unit 100, a part of the radiation light $L_{540}$ travels toward the light guiding member 104. Even in the wavelength converting unit 105, a part of the radiation light $L_{540}$ travels toward the light guiding member 108.

It is possible to impart a diffusion effect to the wavelength converting member 103. For instance, by providing a diffusing surface to or by including fine particles in the wavelength converting member 103, it is possible to achieve the diffusion effect. In a case in which the wavelength converting member 103 has the diffusion effect, scattered light of the excitation light $L_{415}$ and scattered light of the radiation light $L_{540}$ (hereinafter, referred to as 'scattered light $L_{BG}$') are generated.

The scattered light $L_{BG}$ travels in all directions. Therefore, in the wavelength converting unit 100, a part of the scattered light $L_{BG}$ travels toward the light guiding member 104. Even in the wavelength converting unit 105, a part of the scattering light $L_{BG}$ travels toward the light guiding member 108.

It is possible to use a diffusing member instead of the wavelength converting member 103. Although no fluorescent light is generated by the diffusing member, scattered light is generated. The scattered light travels in all directions. Therefore, in the wavelength converting unit 100, a part of the scattered light travels toward the light guiding member 104. Even in the wavelength converting unit 105, a part of the scattered light travels toward the light guiding member 108.

As mentioned above, the diameter of the second light guiding area of the light guiding member 104 is smaller than the diameter of the second light guiding area of the light guiding member 108. Therefore, in the wavelength converting unit 100, it is possible to reduce light incident on the light guiding member as compared to that in the wavelength converting unit 105. As a result, in the wavelength converting unit 100, it is possible to reduce a loss of the illumination light as compared to that in the wavelength converting unit 105.

Moreover, a reflecting surface 102a is formed in the recess. The larger the area of the reflecting surface 102a, the larger is the proportion of the light L1 of the first wavelength band and the proportion of the light L2 of the second wavelength band travelling toward the exit end surface Ro. As shown in FIG. 10B, the reflecting surface 102a does not exist in a range D2 in the wavelength converting unit 105, whereas the reflecting surface 102a does exist at a location corresponding to the range D2 in the wavelength converting unit 100. Therefore, in the wavelength converting unit 100, it is possible to make large the proportion of directing the light L2 of the second wavelength band toward the exit end surface Ro, as compared to that in the wavelength converting unit 105.

In the optical apparatus of the present embodiment, the first light guiding area is disposed on a holding portion side of the second light guiding area. Therefore, it is possible to make the diameter of the second light guiding area extremely small. In this case, it is possible to reduce the proportion of the light L2 of the second wavelength band incident on the second light guiding area, and moreover, it is possible to make large the proportion of directing the light L2 of the second wavelength band toward the exit end surface Ro. As a result, in the optical apparatus of the present embodiment, it is possible to achieve bright illumination light.

(Optical Apparatus 5 of Present Embodiment)

In an optical apparatus of the present embodiment, it is preferable that a light source, a light guiding member, and an optical converting member be disposed in one housing.

For instance, in the optical apparatus 20 shown in FIG. 3, the holding portion 21, the intermediate portion 26, and the tubular portion 22 are connected mechanically. In this case, it can be regarded that one housing is formed by the holding portion 21, the intermediate portion 26, and the tubular portion 22. Therefore, in the optical apparatus 20, the light source 11, the light guiding member 12, and the wavelength converting member 13 are disposed inside one housing.

Even in the optical apparatus 30, the optical apparatus 40, the optical apparatus 50, and the optical apparatus 60, the light source 11, the light guiding member 12, and the wavelength converting member 13 are disposed inside one housing.

(Optical Apparatus 6 of Present Embodiment)

It is preferable that an optical apparatus of the present embodiment include a first housing and a second housing. Moreover, it is preferable that a light source be disposed inside the first housing, a light guiding member and optical converting member be disposed inside the second housing, and the first housing and the second housing be mutually independent.

For instance, in the optical apparatus 70 shown in FIG. 8, it is possible to separate the light source unit 80 from the tubular portion 72 via the connecting portion 79. In this case, it can be regarded that one housing is formed by the light source unit 80.

Moreover, the connecting portion 79, the tubular portion 72, and the holding portion 71 are connected mechanically. In this case, it can be regarded that one housing is formed by the connecting portion 79, the tubular portion 72, and the holding portion 71.

As just described, the optical apparatus 70 includes two housing, or in other words, a first housing and a second housing. In the optical apparatus 70, the light source 11 is disposed inside the first housing. Moreover, the light guiding member 12 and the wavelength converting member 13 are disposed inside the second housing.

The light source unit 80 is connected to the connecting portion 79. Therefore, the light source unit 80 is independent of the connecting portion 79, the tubular portion 72, and the holding portion 71. As just described, in the optical apparatus 70, the first housing and the second housing are mutually independent.

(Optical Apparatus 7 of Present Embodiment)

In the optical apparatus of the present embodiment, it is preferable that following conditional expression (1) be satisfied:

$$LEF1 < \Delta EF \tag{1}$$

where,

LEF1 denotes an optical coupling efficiency of the light guiding member, and is expressed by LEF1=Iout/Iin, $\Delta EF$ denotes a difference in a conversion efficiency of the optical converting member, and is expressed by $\Delta EF=|EFa-EFb|$, Iout denotes an intensity of light incident on the incidence end surface, Iin denotes an intensity of light emanating from the exit end surface, EFa denotes a conversion efficiency when a diameter of the exit end surface is ϕa, EFb denotes a conversion efficiency when the diameter of the exit end surface is ϕb, the conversion efficiency is expressed by Q/P, P denotes an intensity of light irradiated to the optical converting member, Q denotes an intensity of light radiated from the optical converting member, ϕa denotes a diameter of the incidence end surface, and ϕb denotes a diameter of the exit end surface.

In the optical apparatus of the present embodiment, it is preferable that the optical converting member be a wavelength converting member, light of a first wavelength band be emitted from the light source, in the wavelength converting member, light of a second wavelength band be generated from the light of the first wavelength band, light of a wavelength longer than the first wavelength band be included in the light of the second wavelength band, and following conditional expression (1') be satisfied:

$$LEF1 < \Delta EF' \quad (1')$$

where,

LEF1 denotes the optical coupling efficiency of the light guiding member, and is expressed by LEF1=Iout/Iin, ΔEF' denotes a difference in a conversion efficiency of the wavelength converting member, and is expressed by ΔEF'=|EFa'−EFb'|

Iout denotes the intensity of light incident on the incidence end surface,

Iin denotes the intensity of light emanating from the exit end surface,

EFa' denotes a conversion efficiency when a diameter of the exit end surface is ϕa, EFb' denotes a conversion efficiency when the diameter of the exit end surface is ϕb, the conversion efficiency is expressed by Q'/P', P' denotes an intensity of light of the first wavelength band irradiated to the wavelength converting member, Q' denotes one of an intensity of light of the second wavelength band, and a sum of the intensity of the light of the second wavelength band and an intensity of light of the first wavelength band that has transmitted through the wavelength converting member, ϕa denotes the diameter of the incidence end surface, and ϕb denotes the diameter of the exit end surface.

By satisfying conditional expression (1) or conditional expression (1'), it is possible to use efficiently light emitted from the light source.

(Optical Apparatus 8 of Present Embodiment)

In an optical apparatus of the present embodiment, it is preferable that following conditional expression (2) be satisfied:

$$(\phi a/\phi b)^2 \times (NAa/NAb)^2 < 1/2 + (1/2) \times \{(\phi b/(2 \times d))^2 + 1\}^{-1/2} \quad (2)$$

where,

ϕa denotes the diameter of the incidence end surface,

ϕb denotes the diameter of the exit end surface,

NAa denotes a numerical aperture of the incidence end surface,

NAb denotes a numerical aperture of the exit end surface, and d denotes a distance from the exit end surface up to the optical converting member.

In the optical apparatus of the present embodiment, it is preferable that the optical converting member be a wavelength converting member, and following conditional expression (2') be satisfied:

$$(\phi a/\phi b)^2 \times (NAa/NAb)^2 < 1/2 + (1/2) \times \{(\phi b/(2 \times d'))^2 + 1\}^{-1/2} \quad (2')$$

where,

ϕa denotes the diameter of the incidence end surface,

ϕb denotes the diameter of the exit end surface,

NAa denotes the numerical aperture of the incidence end surface,

NAb denotes the numerical aperture of the exit end surface, and d' denotes a distance from the exit end surface up to the wavelength converting member.

By satisfying conditional expression (2) or (2'), it is possible to use efficiently light emitted from the light source.

(Optical Apparatus 9 of Present Embodiment)

In an optical apparatus of the present embodiment, it is preferable that an optical coupler be disposed between the light source and the light guiding member, the optical coupler have a core and a clad, and a diameter of the core be same as the diameter of the incidence end surface.

Figure 11A:
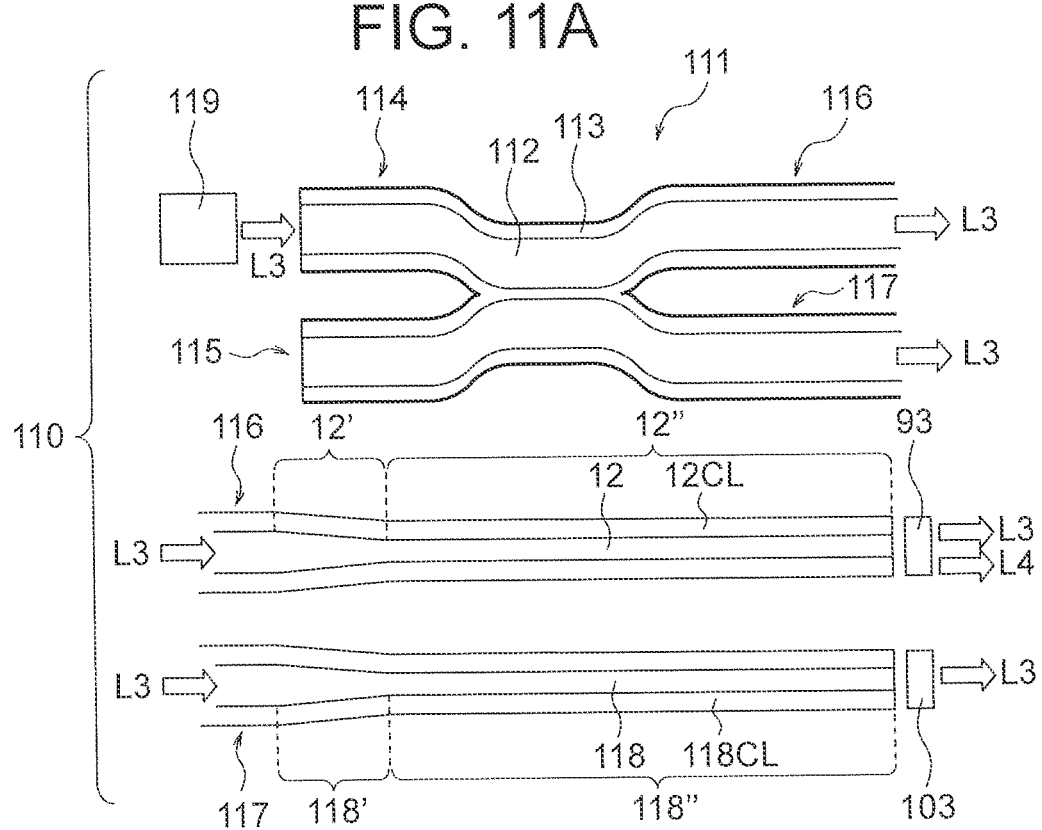
FIG. 11A and FIG. 11B are diagrams showing an optical apparatus of the present embodiment.
Figure 11B:
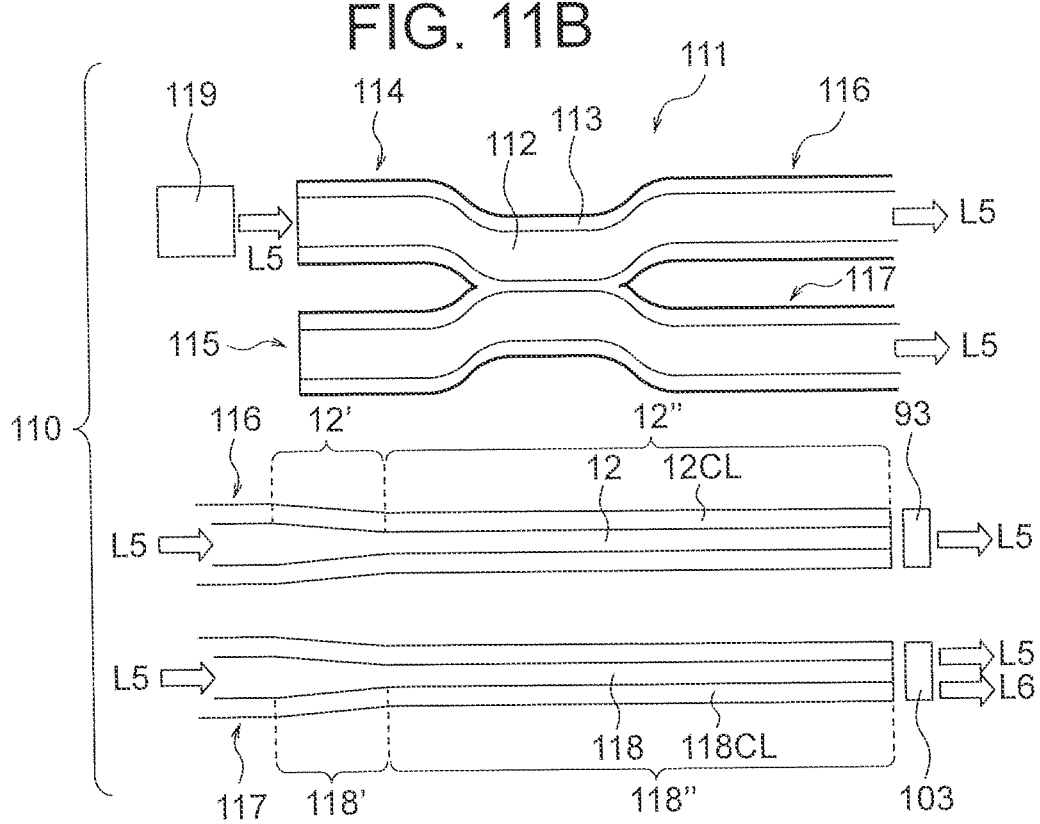

FIG. 11A and FIG. 11B are diagrams showing the optical apparatus of the present embodiment. In the optical apparatus of the present embodiment, it is possible to use two illumination lights of different wavelength bands. FIG. 11A is a diagram showing illumination by one illumination light. FIG. 11B is a diagram showing illumination by the other illumination light.

An optical apparatus 110 includes an optical coupler 111, the light guiding member 12, a light guiding member 118, the wavelength converting member 93, the wavelength converting member 103, and a light source 119.

The light guiding member 118 is same as the light guiding member 12. The light guiding member 118 has a first light guiding area 118' and a second light guiding area 118".

The optical coupler 111 is disposed between the light source 119 and the light guiding member 12 and between the light source 119 and the light guiding member 118.

The optical coupler 111 has a core 112 and a clad 113. The core 112 is formed of a medium having a refractive index higher than 1. The clad 113 has a refractive index lower than the refractive index of the core.

The optical coupler 111 includes an incidence portion 114, an incidence portion 115, an exit portion 116, and an exit portion 117.

It is possible to dispose the light source 119 on an incidence portion 114 side or an incidence portion 115 side. In the optical apparatus 110, the light source 119 is disposed on the incidence portion 114 side.

The light guiding member 12 is positioned on an exit portion 116 side. In the exit portion 116, the core 112 and the light guiding member 12 are formed of a single medium. Therefore, in the exit portion 116, no physical boundary is formed between the core 112 and the light guiding member 12.

A clad 12CL is positioned around the light guiding member 12. In the exit portion 116, even the clad 113 and the clad 12CL are formed of a single medium. Therefore, in the exit portion 116, no physical boundary is formed between the clad 113 and the clad 12CL.

The light guiding member 118 is positioned on an exit portion 117 side. In the exit portion 117, the core 112 and the light guiding member 118 are formed of a single medium. Therefore, in the exit portion 117, no physical boundary is formed between the core 112 and the light guiding member 118.

A clad 118CL is positioned around the light guiding member 118. In the exit portion 117, even the clad 113 and the clad 118CL are also formed of a single medium. Therefore, in the exit portion 117, no physical boundary is formed between the clad 113 and the clad 118CL.

It is possible to form the light guiding member 12 and the clad 12CL by stretching the exit portion 116 while superheating the exit portion 116. It is possible to form the light guiding member 118 and the clad 118CL by stretching while superheating the exit portion 117.

The wavelength converting member 93 is disposed on an exit end surface side of the light guiding member 12. The wavelength converting member 103 is disposed on an exit end surface side of the light guiding member 118.

The largest diameter of the light guiding area 12' is same as a diameter of the core 112 in the incidence portion 114 and a diameter of the core 112 in the incidence portion 115. Moreover, the largest diameter of the first light guiding area 118' is same as a diameter of the core 112 in the incidence portion 114 and a diameter of the core 112 in the incidence portion 115.

As just described, the diameter of the core 112 in the incidence portion 114 and the diameter of the core 112 in the incidence portion 115 indicate the largest diameter of the first light guiding area 12' and the largest diameter of the light guiding area 118'.

It is possible to dispose a lens between the light source 119 and the incidence portion 114 for instance. By disposing a lens, it is possible to make light emitted from the light source 119 incident efficiently on the core 112 of the incidence portion 114.

As mentioned above, the diameter of the core 112 in the incidence portion 114 indicates the largest diameter of the first light guiding area 12' and the largest diameter of the first light guiding area 118'. Therefore, by making the light emitted from the light source 119 incident on the core 112 of the incidence portion 114, it is possible to make the light emitted from the light source 119 incident efficiently on the light guiding member 12 and the light guiding member 118.

Moreover, the diameter of the core 112 in the incidence portion 115 indicates the largest diameter of the first light guiding area 12 and the largest diameter of the first light guiding area 118'. Therefore, by making light emitted from the light source incident on the core 112 of the incidence portion 115, it is possible to make the light emitted from the light source incident efficiently on the light guiding member 12 and the light guiding member 118.

In this case, since it is possible to irradiate bright light to the wavelength converting member 93 and the wavelength converting member 103, it is possible achieve bright illumination light. Therefore, a sharp optical image is formed. Moreover, it is possible to acquire a sharp image from an optical image.

Moreover, a diameter of the second light guiding area 12" and a diameter of the second light guiding area 118" are extremely small. Therefore, in the optical apparatus 110, it is possible to make a thickness of a tubular portion thin. At least a part of the tubular portion is inserted into a body or a metal tube. Accordingly, it is possible to insert the tubular portion easily.

As mentioned above, in the optical coupler 111, the diameter of the core 112 is larger than the diameter of the second light guiding area 12" and the diameter of the second light guiding area 118". Therefore, it is possible to fabricate the optical coupler 111 easily.

The light source 119 is capable of emitting illumination light L3 and illumination light L5. A wavelength band of the illumination light L3 and a wavelength band of the illumination light L5 differ. The illumination light L3 and the illumination light L5 are not emitted simultaneously from the light source 119. When one of the illumination lights is emitted from the light source 119, the other illumination light is not emitted from the light source 119.

In the optical apparatus 110, the wavelength converting member 93 shown in FIG. 9A and the wavelength converting member 103 shown in FIG. 10A are used as the wavelength converting member. Therefore, it is possible to use the excitation light $L_{450}$ as the illumination light L3 and the excitation light $L_{415}$ as the illumination light L5.

Illumination by the illumination light L3 will be described below. As shown in FIG. 11A, the illumination light L3 is emitted from the light source 119. The illumination light L3 is incident on the optical coupler 111 from the incidence portion 114. The illumination light L3 is split into lights that travel along two optical paths. The illumination light L3 that has travelled along one optical path emanates from the exit portion 116. The illumination light L3 that has travelled along the other optical path emanates from the exit portion 117.

The illumination light L3 incident on the light guiding member 12 from the exit portion 116 travels through the light guiding member 12, and is irradiated to the wavelength converting member 93. The illumination light L3 incident on the light guiding member 118 from the exit portion 117 travels through the light guiding member 118, and is irradiated to the wavelength converting member 103.

When the illumination light L3 is irradiated to the wavelength converting member 93, fluorescence L4 is generated from the wavelength converting member 93. As a result, the illumination light L3 and the fluorescence L4 emanate from the wavelength converting member 93. Even when the illumination light L3 is irradiated to the wavelength converting member 103, fluorescence is not generated from the wavelength converting member 103. Accordingly, only the illumination light L3 emanates from the wavelength converting member 103.

In a case in which the excitation light $L_{450}$ is used for the illumination light L3, radiation light $L_{575}$ emanates from the wavelength converting member 93 as the fluorescence $L_4$. As a result, light close to nearly white light emanates from the wavelength converting member 93. Moreover, light of blue color emanates from the wavelength converting member 103. By setting appropriately an optical intensity of the illumination light L3, it is possible to carry out an observation by white light.

Illumination by the illumination light L5 will be described below. As shown in FIG. 11B, the illumination light L5 is emitted from the light source 119. The illumination light L5 is incident on the optical coupler 111. The illumination light L5 travels through the optical coupler 111 in the same manner as the illumination light L3. Therefore, description in detail will be omitted.

Even when the illumination light L5 is irradiated to the wavelength converting member 93, fluorescence is not generated. Therefore, only the illumination light L5 emanates from the wavelength converting member 93. When the illumination light L5 is irradiated to the wavelength converting member 103, fluorescence L6 is generated from the wavelength converting member 103. As a result, the illumination light L5 and the fluorescence L6 emanate from the wavelength converting member 103.

In a case in which the excitation light $L_{415}$ is used for the illumination light L5, the radiation light $L_{540}$ emanates from the wavelength converting member 103. As a result, light close to nearly bluish-green color emanates from the wavelength converting member 103. Moreover, light of purple color emanates from the wavelength converting member 93. By setting appropriately an optical intensity of the illumination light L5, it is possible to carry out NBI (Narrow Band Imaging).

As mentioned above, in the optical apparatus 110, it is possible to achieve bright illumination light. Therefore, in both an observation by white light and the NBI, a sharp optical image is formed. Moreover, it is possible to acquire a sharp image from the optical image.

It is possible to replace one of the wavelength converting member 93 and the wavelength converting member 103 or both the wavelength converting member 93 and the wavelength converting member 103 with a diffusing member. Even in this case, it is possible achieve bright illumination light. Therefore, a sharp optical image is formed. Moreover, it is possible to acquire a sharp image from the optical image.

Figure 12A:
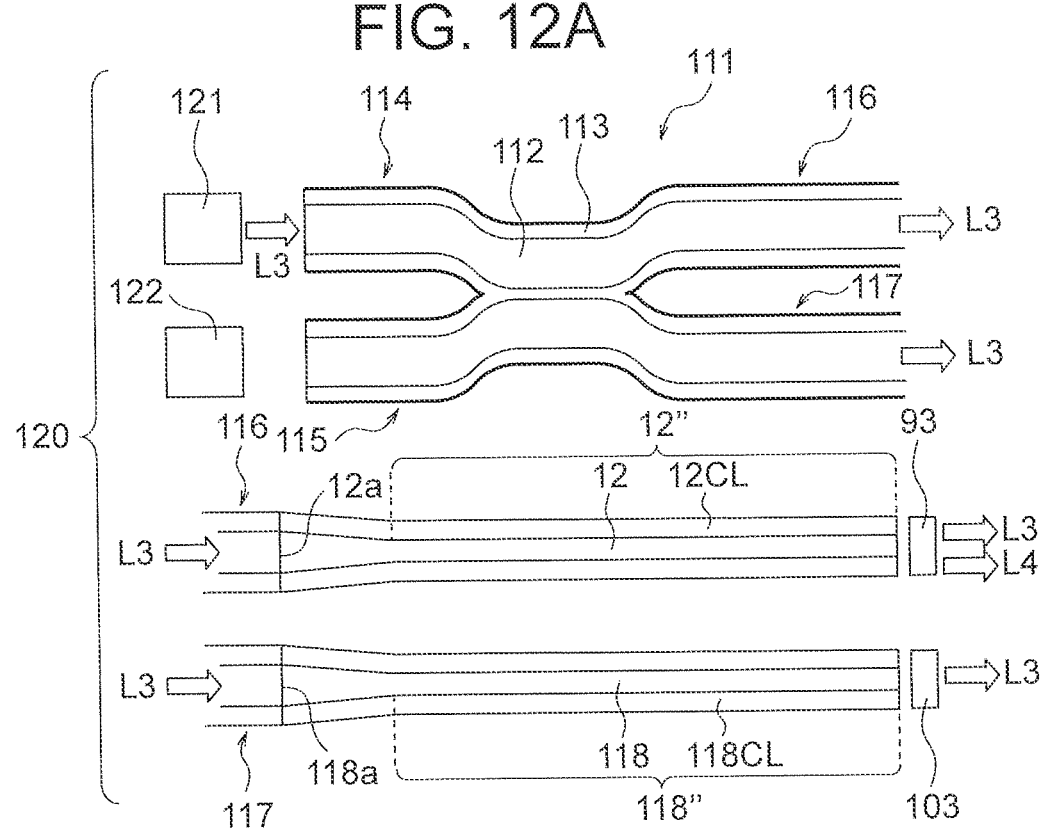
FIG. 12A and FIG. 12B are diagrams showing an optical apparatus of the present embodiment.
Figure 12B:
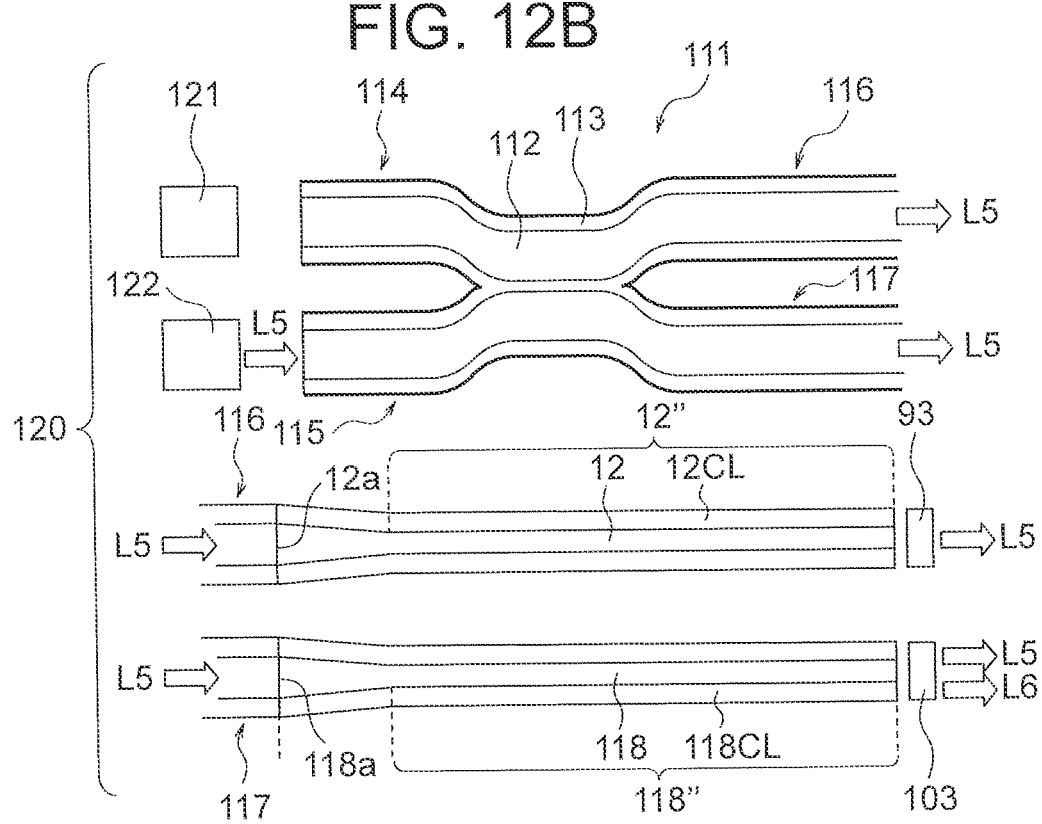

FIG. 12A and FIG. 12B are diagrams showing an optical apparatus of the present embodiment. In the optical apparatus of the present embodiment, it is possible to use two illumination lights of different wavelength bands. FIG. 12A is a diagram showing an illumination by one illumination light. FIG. 12B is a diagram showing an illumination by the other illumination light. Same reference numerals are assigned to components that are same as in FIG. 11A, and description thereof is omitted.

An optical apparatus 120 includes the optical coupler 111, the light guiding member 12, the light guiding member 118, the wavelength converting member 93, the wavelength converting member 103, a light source 121, and a light source 122.

The light source 121 is disposed on the incidence portion 114 side. The light source 122 is disposed on the incidence portion 115 side. The optical coupler 111 is disposed between the light source 121 and the light guiding member 12, and between the light source 122 and the light guiding member 118.

The light guiding member 12 is positioned on the exit portion 116 side. In the exit portion 116, the core 112 and the light guiding member 12 are not formed of a single medium. Therefore, in the exit portion 116, a physical boundary is formed between the core 112 and the light guiding member 12.

In the exit portion 116, even the clad 113 and the clad 12CL are not formed of a single medium. Therefore, in the exit portion 116, a physical boundary is formed between the clad 113 and the clad 12CL.

The light guiding member 118 is positioned on the exit portion 117 side. In the exit portion 117, the core 112 and the light guiding member 118 are not formed of a single medium. Therefore, in the exit portion 117, a physical boundary is formed between the core 112 and the light guiding member 118.

In the exit portion 117, even the clad 113 and the clad 118CL are not formed of a single medium. Therefore, in the exit portion 117, a physical boundary is formed between the clad 113 and the clad 118CL.

The diameter of the incidence end portion 12a is same as the diameter of core 112. Moreover, a diameter of the incidence end surface 118a is same as the diameter of the core 112. As just described, the diameter of the core 112 indicates the diameter of the incidence end surface 12a and the diameter of the incidence end surface 118a.

It is possible to dispose a lens between the light source 121 and the incidence portion 114 for instance. By disposing the lens, it is possible to make light emitted from the light source 121 incident efficiently on the core 112 of the incidence portion 114.

It is possible to dispose a lens between the light source 122 and the incidence portion 114 for instance. By disposing the lens, it is possible to make light emitted from the light source 122 incident efficiently on the core 112 of the incidence portion 115.

As mentioned above, the diameter of the core 112 indicates the diameter of the incidence end surface 12a and the diameter of the incidence end surface 118a. Therefore, by making the light emitted from the light source 121 incident on the core 112 of the incidence portion 114, it is possible to make the light emitted from the light source 121 incident efficiently on the light guiding member 12 and the light guiding member 118.

Moreover, by making the light emitted from the light source 122 incident on the core 112 of the incidence portion 115, it is possible to make the light emitted from the light source 122 incident efficiently on the light guiding member 12 and the light guiding member 118.

In this case, since it is possible to irradiate bright light to the wavelength converting member 93 and the wavelength converting member 103, it is possible to achieve bright illumination light. Therefore, a sharp optical image is formed. Moreover, it is possible to acquire a sharp image from the optical image.

Moreover, the diameter of the second light guiding area 12" and the diameter of the second light guiding area 118" are extremely small. Therefore, in the optical apparatus 120, it is possible to make a thickness of a tubular portion thin. At least a part of the tubular portion is inserted into a body or a metal tube. Accordingly, it is possible to insert the tubular portion easily.

As mentioned above, in the optical coupler 111, the diameter of the core 112 is larger than the diameter of the second light guiding area 12" and the diameter of the second light guiding area 118". Therefore, it is possible to fabricate the optical coupler 111 easily.

The light source 121 is capable of emitting the illumination light L3. The light source 122 is capable of emitting the illumination light L5. The illumination light L3 and the illumination light L5 are not emitted simultaneously. When one illumination light is being emitted from the light source, the other illumination light is not emitted from the light source.

As shown in FIG. 12A, in a case in which the illumination light L3 is emitted from the light source 121, the illumination light L3 and the fluorescence L4 emanate from the wavelength converting member 93, and only the illumination light L3 emanates from the wavelength converting member 103.

As shown in FIG. 12B, in a case in which the illumination light L5 is emitted from the light source 122, only the illumination light L5 emanates from the wavelength converting member 93, and the illumination light L5 and the fluorescence L6 emanate from the wavelength converting member 103.

As a result, in the optical apparatus 120, it is possible to achieve bright light similarly as in the optical apparatus 110. Therefore, in both the observation by the white light and the NBI, a sharp optical image is formed. Moreover, it is possible to acquire a sharp image from the optical image.

(Optical Apparatus 10 of Present Embodiment)

In an optical apparatus of the present embodiment, it is preferable that following conditional expression (3) be satisfied:

$$LEF1cou < \Delta EF \quad (3)$$

where,

LEF1cou=LEF1+ΔLEFcou,

LEF1 denotes the optical coupling efficiency of the light guiding member, and is expressed by LEF1=Iout/Iin, ΔLEFcou denotes a difference in an optical coupling efficiency of the optical coupler, and is expressed by ΔLEFcou=|LEFcoua−LEFcoub|, Iout denotes the intensity of light incident on the incidence end surface, Iin denotes the intensity of light emanating from the exit end surface, LEFcoua denotes an optical coupling efficiency when a diameter of the core is ϕa, LEFcoub denotes an optical coupling efficiency when a diameter of the core is ϕb, ΔEF denotes the difference in the conversion efficiency of the optical converting member, and is expressed by ΔEF=|EFa−EFb|, EFa denotes the conversion efficiency when the diameter of the exit end surface is ϕa, EFb denotes the conversion efficiency when the diameter of the exit end surface is ϕb, P denotes the intensity of light irradiated to the optical converting member, Q denotes the intensity of light radiated from the optical converting member, ϕa denotes the diameter of the incidence end surface, and ϕb denotes the diameter of the exit end surface.

In the optical apparatus of the present embodiment, it is preferable that the optical converting member be the wavelength converting member, light of a first wavelength band be emitted from the light source, in the wavelength converting member, light of a second wavelength band be generated from the light of the first wavelength band, light of a wavelength longer than the first wavelength band be included in the light of the second wavelength band, and following conditional expression (3') be satisfied:

$$LEF1cou < \Delta EF' \quad (3')$$

where,

LEF1cou=LEF1+ΔLEFcou,

LEF1 denotes the optical coupling efficiency of the light guiding member, and is expressed by LEF1=Iout/Iin, ΔLEFcou denotes the difference in an optical coupling efficiency of the optical coupler, and is expressed by ΔLEFcou=|LEFcoua−LEFcoub|

Iout denotes the intensity of light incident on the incidence end surface,

Iin denotes the intensity of light emanating from the exit end surface,

LEFcoua denotes the optical coupling efficiency when a diameter of the core is ϕa, LEFcoub denotes the optical coupling efficiency when the diameter of the core is ϕb, ΔEF' denotes the difference in the conversion efficiency of the wavelength converting member, and is expressed by ΔEF'=|EFa'−EFb'|, EFa' denotes the conversion efficiency when a diameter of the exit end surface is ϕa, EFb' denotes the conversion efficiency when a diameter of the exit end surface is ϕb, the conversion efficiency is expressed by Q'/P', P' denotes the intensity of light of the first wavelength band irradiated to the wavelength converting member, Q' denotes one of an intensity of light of the second wavelength band, and a sum of the intensity of the light of the second wavelength band and an intensity of light of the first wavelength band that has transmitted through the wavelength converting member, ϕa denotes the diameter of the incidence end surface, and ϕb denotes the diameter of the exit end surface.

By satisfying conditional expression (3) or conditional expression (3'), it is possible to use effectively light emitted from the light source.

(Optical Apparatus 11 of Present Embodiment)

In an optical apparatus of the present embodiment, it is preferable that a pair of optical connectors be disposed between the light source and the light guiding member, the optical connector have a light guiding member and a holding member, and a diameter of the light guiding member of the optical connector be same as the diameter of the incidence end surface.

Figure 13A:
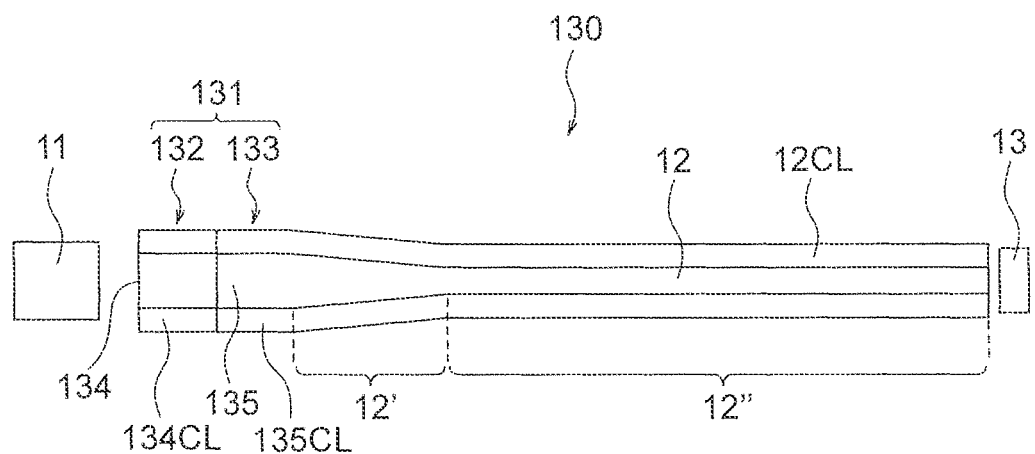
FIG. 13A and FIG. 13B are diagrams showing an optical apparatus of the present embodiment.
Figure 13B:
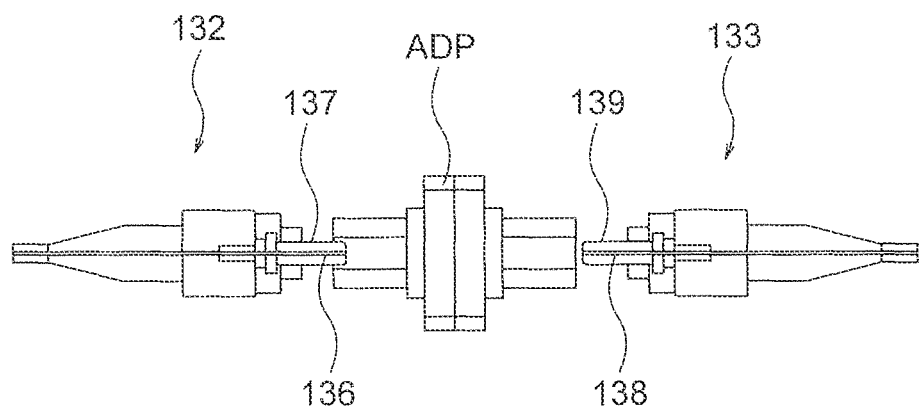

FIG. 13A and FIG. 13B are diagrams showing the optical apparatus of the present embodiment. FIG. 13A is a diagram showing a configuration of the optical apparatus, and FIG. 13B is a diagram showing a configuration of the optical connector. Same reference numerals are assigned to components that are same as in FIG. 2A, and description thereof is omitted.

As shown in FIG. 13A, an optical apparatus 130 includes the light source 11, a pair of optical connectors 131, the light guiding member 12, and the wavelength converting member 13. The pair of optical connectors 131 includes an optical connector 132 and an optical connector 133.

The pair of optical connectors 131 is positioned on a light source 11 side of the light guiding member 12. Accordingly, the pair of optical connectors 131 is disposed between the light source 11 and the light guiding member 12.

The optical connector 132 is positioned on the light source 11 side, and the optical connector 133 is positioned on the light guiding member 12 side. The optical connector 132 includes a light guiding member 134 and a clad 134CL. The optical connector 133 includes a light guiding member 135 and a clad 135CL. The light guiding member 134 and the light guiding member 135 are formed of a medium having a refractive index higher than 1.

A specific structure of the pair of optical connectors 131 will be described below. As shown in FIG. 13B, the optical connector 132 includes an optical fiber 136 and a holding member 137. The optical fiber 136 includes the light guiding member 134 and the clad 134CL.

The optical connector 133 includes an optical fiber 138 and a holding member 139. The optical fiber 138 includes the light guiding member 135 and the clad 135CL.

The holding member 137 and the holding member 139 are connected via an optical adapter ADP. A through hole is formed in the optical adapter ADP. By inserting the holding member 137 and the holding member 139 into the through hole, it is possible to connect the light guiding member 134 and the light guiding member 135.

Description will be made returning back to FIG. 13A. The clad 134CL is positioned around the light guiding member 134. The clad 135CL is positioned around the light guiding member 135.

The light guiding member 135 and the light guiding member 12 are formed of a single medium. Accordingly, no physical boundary is formed between the light guiding member 135 and the light guiding member 12. The clad 135CL and the clad 12CL are also formed of a single medium. Accordingly, no physical boundary is formed between the clad 135CL and the clad 12CL.

The wavelength converting member 13 is disposed on an exit end surface side of the light guiding member 12.

The largest diameter of the first light guiding area 12' is same as a diameter of the light guiding member 135. The diameter of the light guiding member 135 is same as a diameter of the light guiding member 134. Accordingly, the largest diameter of the first light guiding area 12' is same as the diameter of the light guiding member 134. As just described, the diameter of the light guiding member 134 indicates the largest diameter of the first light guiding area 12'.

It is possible to dispose a lens between the light source 11 and the light guiding member 134 for instance. By disposing the lens, it is possible to make the light emitted from the light source 11 incident efficiently on the light guiding member 134.

As mentioned above, the diameter of the light guiding member 134 indicates the largest diameter of the first light guiding area 12'. Accordingly, by making the light emitted from the light source 11 incident on the light guiding member 134, it is possible to make the light emitted from the light source 11 incident efficiently on the light guiding member 12.

In this case, since it is possible to illuminate bright light on the wavelength converting member 13, it is possible to achieve bright illumination light. Therefore, a sharp optical image is formed. Moreover, it is possible to acquire a sharp image from the optical image.

It is possible to replace the wavelength converting member 13 with a diffusing member. Even in this case, it is possible to achieve bright illumination light. Therefore, a sharp optical image is formed. Moreover, it is possible to acquire a sharp image from the optical image.

Moreover, the diameter of the second light guiding area 12" is extremely small. Therefore, in the optical apparatus 130, it is possible to make a thickness of a tubular portion thin. At least a part of the tubular portion is inserted into a body or a metal tube. Accordingly, it is possible to insert the tubular portion easily.

The optical apparatus 130 includes the pair of optical connectors 131. In this case, it is possible to divide the optical apparatus 130 into two housings by the optical adapter ADP for example. Therefore, with respect to one housing, the other housing can be disposed at various locations.

The one housing includes the light source 11. The other housing includes the light guiding member 12 and the wavelength converting member 13. The two housings are connected by the optical connector 132 and the optical connector 133.

By connecting the optical connector 132 and the optical connector 133, the light guiding member 134 and the light guiding member 135 are connected. As a result, the light emitted from the light source 11 is propagated by the light guiding member 134 and the light guiding member 135. When there is a position shift between the light guiding member 134 and the light guiding member 135 after the light guiding member 134 and the light guiding member 135 are connected, a loss of light occurs.

In the optical apparatus 130, the diameter of the light guiding member 134 and the diameter of the light guiding member 135 are larger than the diameter of the second light guiding area 12". Therefore, even when the position shift occurs between the light guiding member 134 and the light guiding member 135, it is possible to reduce the loss of light at the time of connection.

Figure 14:
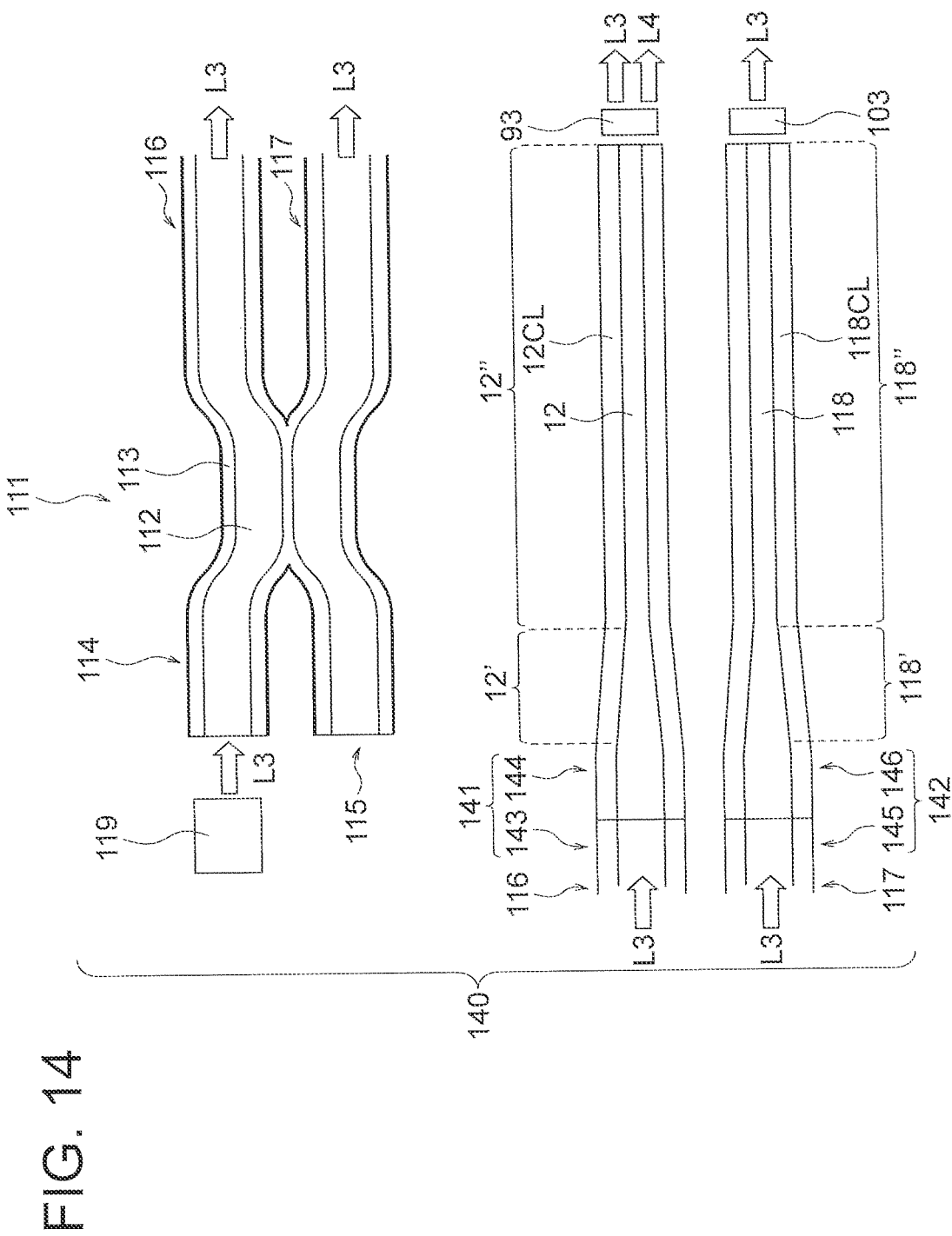
FIG. 14 is a diagram showing an optical apparatus of the present embodiment.

FIG. 14 is a diagram showing an optical apparatus of the present embodiment. Same reference numerals are assigned to components that are same as in FIG. 11A, and description thereof is omitted.

An optical apparatus 140 includes the optical coupler 111, a pair of optical connectors 141, a pair of optical connectors 142, the light guiding member 12, the light guiding member 118, the wavelength converting member 93, the wavelength converting member 103, and the light source 119.

The pair of optical connectors 141 includes an optical connector 143 and an optical connector 144. The pair of optical connectors 142 includes an optical connector 145 and an optical connector 146.

The pair of optical connectors 141 is positioned on a light source 119 side of the light guiding member 12. Accordingly, the pair of optical connectors 141 is disposed between the light source 119 and the light guiding member 12.

The pair of optical connectors 142 is positioned on a light source 119 side of the light guiding member 118. Accordingly, the pair of optical connectors 142 is disposed between the light source 119 and the light guiding member 118.

The optical coupler 111 and the pair of optical connectors 141 are disposed between the light source 119 and the light guiding member 12. The optical coupler 111 is positioned on a light source 119 side of the pair of optical connectors 141.

The optical coupler 111 and the pair of optical connectors 142 are disposed between the light source 119 and the light guiding member 118. The optical coupler 111 is disposed on a light source 119 side of the pair of optical connectors 142.

The optical connector 143 is positioned on an exit portion 116 side. In the exit portion 116, a light guiding member of the optical connector 143 and the core 112 are formed of a single medium. Accordingly, in the exit portion 116, no physical boundary is formed between the light guiding member of the optical connector 143 and the core 112.

The optical connector 144 is positioned adjacent to the optical connector 143. The light guiding member of the optical connector 144 and the light guiding member 12 are formed of a single medium. Accordingly, no physical boundary is formed between the light guiding member of the optical connector 144 and the light guiding member 12.

The optical connector 145 is positioned on the exit portion 117 side. In the exit portion 117, the light guiding member of the optical connector 145 and the core 112 are formed of a single medium. Accordingly, in the exit portion 117, no physical boundary is formed between the light guiding member of the optical connector 145 and the core 112.

The optical connector 146 is positioned adjacent to the optical connector 145. A light guiding member of the optical connector 146 and the light guiding member 118 are formed of a single medium. Accordingly, no physical boundary is formed between the light guiding member of the optical connector 146 and the light guiding member 118.

The largest diameter of the first light guiding area 12' is same as a diameter of the light guiding member of the optical connector 144. The diameter of the light guiding member of the optical connector 144 is same as a diameter of the light guiding member of the optical connector 143.

Furthermore, the diameter of the light guiding member of the optical connector 143 is same as the diameter of the core 112 in the incidence portion 114, and the diameter of the core 112 in the incidence portion 115. Accordingly, the largest diameter of the first light guiding area 12' is same as the diameter of the core 112 in the incidence portion 114 and the diameter of the core 112 in the incidence portion 115.

When the diameter of the light guiding member of the optical connector 143 and the diameter of the core 112 in the incidence portion 114 differ, a loss of quantity of light occurs between the light guiding member of the optical connector 143 and the core 112 in the incidence portion 114. As a result, the coupling efficiency is degraded.

However, when the loss of quantity of light or a degradation of coupling efficiency is of a magnitude of an acceptable degree, the diameter of the light guiding member of the optical connector 143 and the diameter of the core 112 in the incidence portion 114 can be regarded as same. Similar is a case of the diameter of the light guiding member of the optical connector 143 and the diameter of the core 112 in the incidence portion 115. Moreover, similar is true for a connection with the optical coupler shown in FIG. 12B.

The largest diameter of the first light guiding area 118' is same as a diameter of the light guiding member of the optical connector 146. The diameter of the light guiding member of the optical connector 146 is same as a diameter of a light guiding member of the optical connector 145.

Furthermore, the diameter of the light guiding member of the optical connector 145 is same as the diameter of the core 112 in the incidence portion 114 and the diameter of the core 112 in the incidence portion 115. Accordingly, the largest diameter of the first light guiding area 118' is same as the diameter of the core 112 in the incidence portion 114 and the diameter of the core 112 in the incidence portion 115.

As just described, the diameter of the core 112 in the incidence portion 114 and the diameter of the core 112 in the incidence portion 115 indicate the largest diameter of the first light guiding area 12' and the largest diameter of the first light guiding area 118'.

Accordingly, by making light emitted from the light source 119 incident on the core 112 of the incidence portion 114, it is possible to make the light emitted from the light source 119 incident efficiently on the light guiding member 12 and the light guiding member 118.

Moreover, by making light emitted from the light source incident on the core 112 of the incidence portion 115, it is possible to make the light emitted from the light source incident efficiently on the light guiding member 12 and the light guiding member 118.

In this case, since it is possible to irradiate bright light to the wavelength converting member 93 and the wavelength converting member 103, it is possible to achieve bright illumination light. Therefore, a sharp optical image is formed. Moreover, it is possible to acquire a sharp image from the optical image.

In FIG. 14, an appearance when the illumination light L3 is emitted from the light source 119 is shown. As mentioned above, the light source 119 is capable of emitting not only the illumination light L3 but also the illumination light L5. Accordingly, in the optical apparatus 140, it is possible to carry out an observation by white light and the NBI. In both cases, it is possible to achieve bright illumination light.

It is possible to replace one of the wavelength converting member 93 and the wavelength converting member 103 or both the wavelength converting member 93 and the wavelength converting member 103 with a diffusing member. Even in this case, it is possible to achieve bright illumination light.

The optical apparatus 140 includes the pair of optical connectors. Therefore, it is possible to divide the apparatus into two housings. In this case, with respect to one housing, the other housing can be disposed at various locations. The two housings are connected by the pair of optical connectors 141 and the pair of optical connectors 142.

In the optical apparatus 140, a loss of light at the time of connecting is small, and it is possible to achieve bright illumination light. Therefore, a sharp optical image is formed. Moreover, it is possible to acquire a sharp image from the optical image.

Figure 15:
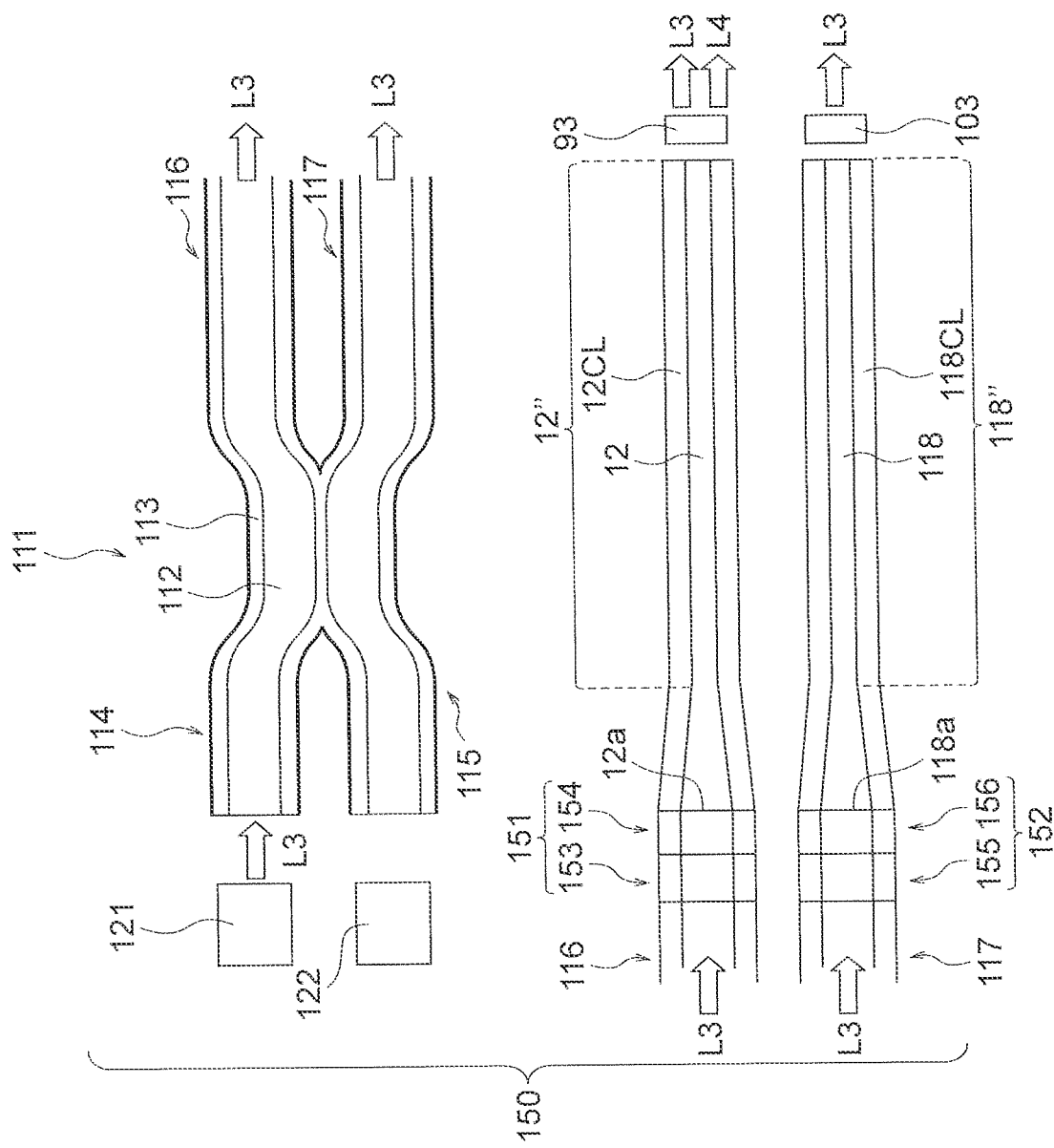
FIG. 15 is a diagram showing an optical apparatus of the present embodiment.

FIG. 15 is a diagram showing an optical apparatus of the present embodiment. Same reference numerals are assigned to components that are same as in FIG. 12A, and description thereof is omitted.

An optical apparatus 150 includes the optical coupler 111, a pair of optical connectors 151, a pair of optical connectors 152, the light guiding member 12, the light guiding member 118, the wavelength converting member 93, the wavelength converting member 103, the light source 121 and the light source 122.

The pair of optical connectors 151 includes an optical connector 153 and an optical connector 154. The pair of optical connectors 152 includes an optical connector 155 and an optical connector 156.

The pair of optical connectors 151 is positioned on a light source 121 side of the light guiding member 12. Accordingly, the pair of optical connectors 151 is disposed between the light source 121 and the light guiding member 12.

The pair of optical connectors 152 is positioned on a light source 122 side of the light guiding member 118. Accordingly, the pair of optical connectors 152 is disposed between the light source 122 and the light guiding member 118.

The optical coupler 111 and the pair of optical connectors 151 are disposed between the light source 121 and the light guiding member 12. The optical coupler 111 is positioned on a light source 121 side of the pair of optical connectors 151.

The optical coupler 111 and the pair of optical connectors 152 are disposed between the light source 122 and the light guiding member 118. The optical coupler 111 is positioned on a light source 122 side of the pair of optical connectors 152.

The optical connector 153 is positioned on the exit portion 116 side. In the exit portion 116, a light guiding member of the optical connector 153 and the core 112 are not formed of a single medium. Accordingly, a physical boundary is formed between the light guiding member of the optical connector 153 and the core 112.

The optical connector 154 is positioned adjacent to the optical connector 153. A light guiding member of the optical connector 154 and the light guiding member 12 are not formed of a single medium. Accordingly, a physical boundary is formed between the light guiding member of the optical connector 154 and the light guiding member 12.

The optical connector 155 is positioned on the exit portion 117 side. A light guiding portion of the optical connector 155 and the core 112 are not formed of a single medium. Accordingly, a physical boundary is formed between the light guiding member of the optical connector 155 and the core 112.

The optical connector 156 is positioned adjacent to the optical connector 155. A light guiding member of the optical connector 156 and the light guiding member 118 are not formed of a single medium. Accordingly, a physical boundary is formed between the light guiding member of the optical connector 156 and the light guiding member 118.

The diameter of the incidence end surface 12a is same as a diameter of the light guiding member of the optical connector 154. The diameter of the light guiding member of the optical connector 154 is same as a diameter of the light guiding member of the optical connector 153.

Furthermore, the diameter of the light guiding member of the optical connector 153 is same as the diameter of the core 112. Accordingly, the largest diameter of the incidence end surface 12a is same as the diameter of the core 112.

The diameter of the incidence end surface 118a is same as a diameter of the light guiding member of the optical connector 156. The diameter of the light guiding member of the optical connector 156 is same as a diameter of the light guiding member of the optical connector 155.

Furthermore, the diameter of the light guiding member of the optical connector 155 is same as the diameter of the core 112. Accordingly, the diameter of the incidence end surface 118a is same as the diameter of the core 112.

As just described, the diameter of the core 112 indicates the largest diameter of the incidence end surface 12a and the diameter of the incidence end surface 118a.

Accordingly, by making light emitted from the light source 121 incident on the core 112 of the incidence portion 114, it is possible to make the light emitted from the light source 121 incident efficiently on the light guiding member 12 and the light guiding member 118.

Moreover, by making light emitted from the light source 122 incident on the core of the incidence portion 115, it is possible to make the light emitted from the light source 122 incident efficiently on the light guiding member 12 and the light guiding member 118.

In this case, since it is possible to irradiate bright light to the wavelength converting member 93 and the wavelength converting member 103, it is possible to achieve bright illumination light. Therefore, a sharp optical image is formed. Moreover, it is possible to acquire a sharp image from the optical image.

In FIG. 15, an appearance when the illumination light L3 is emitted from the light source 121 is shown. As mentioned above, the illumination light L5 is emitted from the light source 122. Accordingly, in the optical apparatus 150, it is possible to carry out an observation by white light and the NBI. In both cases, it is possible to achieve bright illumination light.

It is possible to replace one of the wavelength converting member 93 and the wavelength converting member 103 or both the wavelength converting member 93 and the wavelength converting member 103 with a diffusing member. Even in this case, it is possible to achieve bright illumination light.

The optical apparatus 150 includes the pair of optical connectors. Therefore, it is possible to divide the apparatus into two housings. In this case, with respect to one housing, the other housing can be disposed at various locations. The two housings are connected by the pair of optical connectors 151 and the pair of optical connectors 152.

In the optical apparatus 150, a loss of light at the time of connecting is small, and it is possible to achieve bright illumination light. Therefore, a sharp optical image is formed. Moreover, it is possible to acquire a sharp image from the optical image.

(Optical Apparatus 12 of Present Embodiment)

In an optical apparatus of the present embodiment, it is preferable that following conditional expression (4) be satisfied:

$$LEF1cne < \Delta EF \qquad (4)$$

where,

LEF1cne=LEF1+ΔLEFcne,

LEF1 denotes the optical coupling efficiency of the light guiding member, and is expressed by LEF1=Iout/Iin, ΔLEFcne denotes a difference in an optical coupling efficiency of the optical connector, and is expressed by ΔLEFcne=|LEFcnea−LEFcneb|

Iout denotes the intensity of light incident on the incidence end surface,

Iin denotes the intensity of light emanating from the exit end surface,

LEFcnea denotes an optical coupling efficiency when a diameter of the light guiding member of the optical connector is $\phi a$, LEFcneb denotes an optical coupling efficiency when a diameter of the light guiding member of the optical connector is $\phi b$, ΔEF denotes the difference in the conversion efficiency of the optical converting member, and is expressed by ΔEF=|EFa−EFb|, EFa denotes the conversion efficiency when the diameter of the exit end surface is $\phi a$, EFb denotes the conversion efficiency when the diameter of the exit end surface is $\phi b$, the conversion efficiency is expressed by Q/P, P denotes the intensity of light irradiated to the optical converting member, Q denotes the intensity of light radiated from the optical converting member, $\phi a$ denotes the diameter of the incidence end surface, and $\phi b$ denotes the diameter of the exit end surface.

In the optical apparatus of the present embodiment, it is preferable that the optical converting member be the wavelength converting member, light of a first wavelength band be emitted from the light source, in the wavelength converting member, light of second wavelength band be generated from the light of the first wavelength band, light of a wavelength longer than the first wavelength band be included in the light of the second wavelength band, and following conditional expression (4') be satisfied:

$$LEF1cne < \Delta EF' \qquad (4')$$

where,

LEF1cne=LEF1+ΔLEFcne,

LEF1 denotes the optical coupling efficiency of the light guiding member, and is expressed by LEF1=Iout/Iin, ΔLEFcne denotes the difference in the optical coupling efficiency of the optical connector, and is expressed by ΔLEFcne=|LEFcnea−LEFcneb|

Iout denotes the intensity of light incident on the incidence end surface,

Iin denotes the intensity of light emanating from the exit end surface,

LEFcnea denotes the optical coupling efficiency when the diameter of the light guiding member of the optical connector is φa, LEFcneb denotes the optical coupling efficiency when the diameter of the light guiding member of the optical connector is φb, ΔEF' denotes the difference in the conversion efficiency of the wavelength converting member, and is expressed by ΔEF'=|EFa'−EFb'|, EFa' denotes the conversion efficiency when the diameter of the exit end surface is φa, EFb' denotes the conversion efficiency when the diameter of the exit end surface is φb, the conversion efficiency is expressed by Q'/P', P' denotes the intensity of the light of the first wavelength band irradiated to the wavelength converting member, Q' denotes one of an intensity of light of the second wavelength band, and a sum of the intensity of the light of the second wavelength band and an intensity of light of the first wavelength band that has transmitted through the wavelength converting member, φa denotes a diameter of the incidence end surface, and φb denotes a diameter of the exit end surface.

By satisfying conditional expression (4) or conditional expression (4'), it is possible to use efficiently light emitted from the light source.

The light of the first wavelength band irradiated to the wavelength converting member is light emanated from the exit end surface of the light guiding member. Accordingly, P' in conditional expression (1'), conditional expression (3'), and conditional expression (4') can be said to be 'intensity of light of the first wavelength band emanated from the exit end surface of the light guiding member'.

As shown in FIG. 9A, the wavelength converting unit has the incidence end surface Ri and the exit end surface Ro. In the wavelength converting unit, light emanated from the exit end surface Ro is used as the illumination light.

As mentioned above, in the wavelength converting member, the light of the second wavelength band is generated from the light of the first wavelength band. The light of the second wavelength band being fluorescence, travels in all directions.

The wavelength converting member has a surface positioned on an incidence end surface Ri side and a surface positioned on an exit end surface Ro side. Accordingly, in the wavelength converting member, the light of the second wavelength band emanates from the surface positioned on the incidence end surface Ri side and the surface positioned on the exit end surface Ro side.

Q' in conditional expression (1'), conditional expression (3'), and conditional expression (4') is the intensity of light that can be used as the illumination light. As mentioned above, the light emanated from the exit end surface Ro is the light that can be used as the illumination light. The light emanated from the exit end surface Ro is the light emanated from the surface positioned on the exit end surface Ro side. Accordingly, the light emanated from the surface positioned on the exit end surface Ro side is the light that can be used as the illumination light.

The intensity of light of the second wavelength band in Q' implies the intensity of light emanated from the surface positioned on the exit end surface Ro side. Similar is true for the intensity of light of the first wavelength band.

(Optical Apparatus 13 of Present Embodiment)

It is preferable that an optical apparatus of the present embodiment include a housing which has the holding portion and the tubular portion, and the light source, the pair of optical connectors, the light guiding member, and the optical converting member be disposed in the housing.

Figure 16:
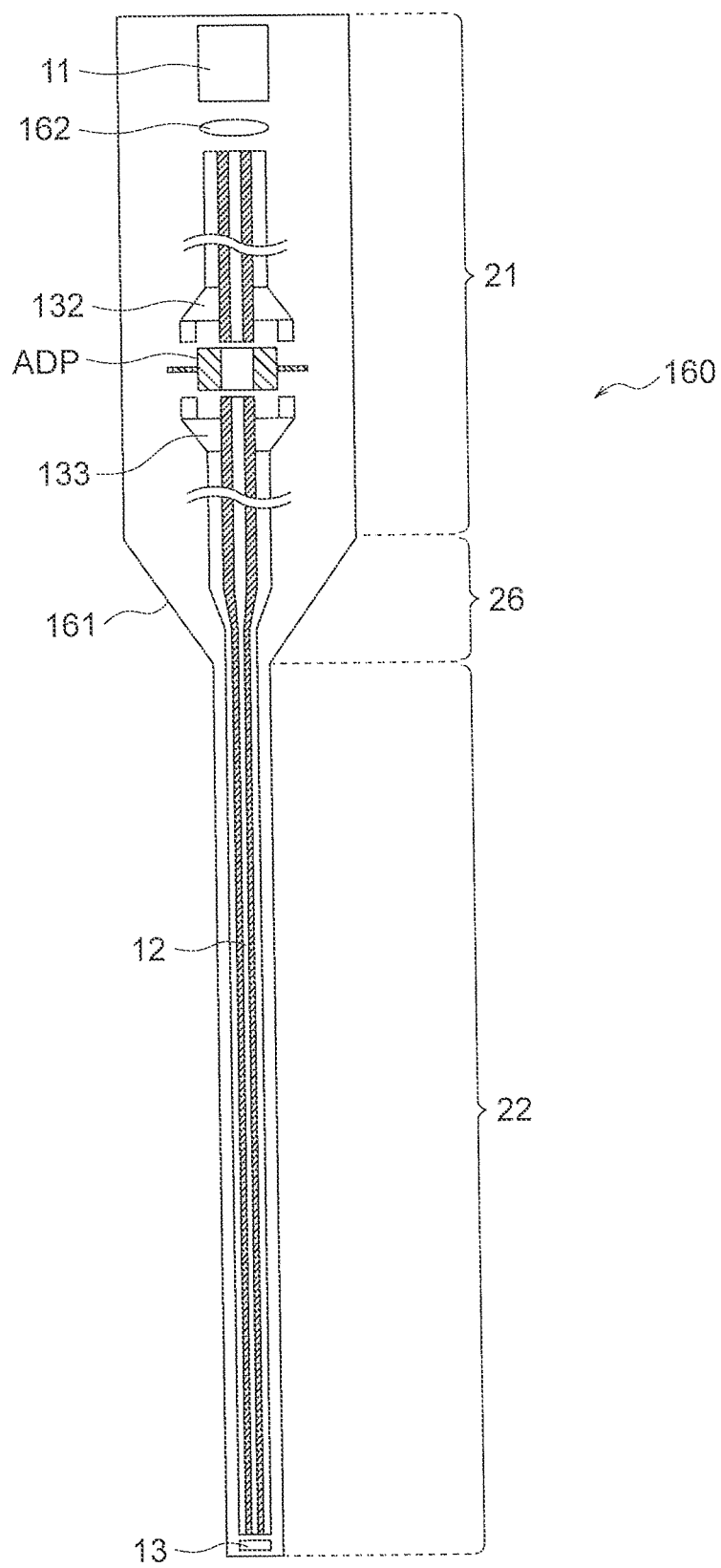
FIG. 16 is a diagram showing an optical apparatus of the present embodiment.

FIG. 16 is a diagram showing the optical apparatus of the present embodiment. Same reference numerals are assigned to components that are same as in FIG. 3A and components that are same as in FIG. 13A, and description thereof is omitted.

An optical apparatus 160 is a wireless endoscope. The optical apparatus 160 includes a housing 161. The housing 161 includes the holding portion 21, the tubular portion 22, and the intermediate portion 26. The intermediate portion 26 can be provided according to the requirement.

The light source 11, a lens 162, the optical connector 132, the optical adapter ADP, the optical connector 133, the light guiding member 12, and the wavelength converting member 13 are disposed at an interior of the housing 161. A pair of optical connectors is formed by the optical connector 132 and the optical connector 133.

Light emitted from the light source 11 is focused by the lens 162. The light guiding member of the optical connector 132 is disposed at a focusing position. Accordingly, it is possible to make the light emitted from the light source 11 incident on the light guiding member of the optical connector 132.

In FIG. 16, the optical connector 132 and the optical connector 133 are not connected to the optical adapter ADP. By connecting the optical connector 132 and the optical connector 133 to the optical adapter ADP, the light guiding member of the optical connector 132 and the light guiding member of the optical connector 133 are connected. As a result, it is possible to make light that is incident on the light guiding member of the optical connector 132 incident on the light guiding member of the optical connector 133.

The light guiding member of the optical connector 133 and the light guiding member 12 are formed of a single medium. Accordingly, light emanated from the optical connector 133 is incident on the light guiding member 12. Light incident on the light guiding member 12 emanates from the light guiding member 12. Light emanated from the light guiding member 12 is irradiated to the wavelength converting member 13.

In the optical apparatus 160, the pair of connectors is disposed at the interior of the one housing 161. Accordingly, at the time of fabricating, it is possible to fabricate by separating apart a light source 11 side and a light guiding member 12 side with the connector as a boundary between the two sides. Therefore, it is possible to increase a degree of freedom of fabricating. Moreover, repairing becomes easy.

(Optical Apparatus 14 of Present Embodiment)

It is preferable that an optical apparatus of the present embodiment include a first housing and a second housing, and the first housing have one optical connector, and the second housing have the other optical connector.

Figure 17:
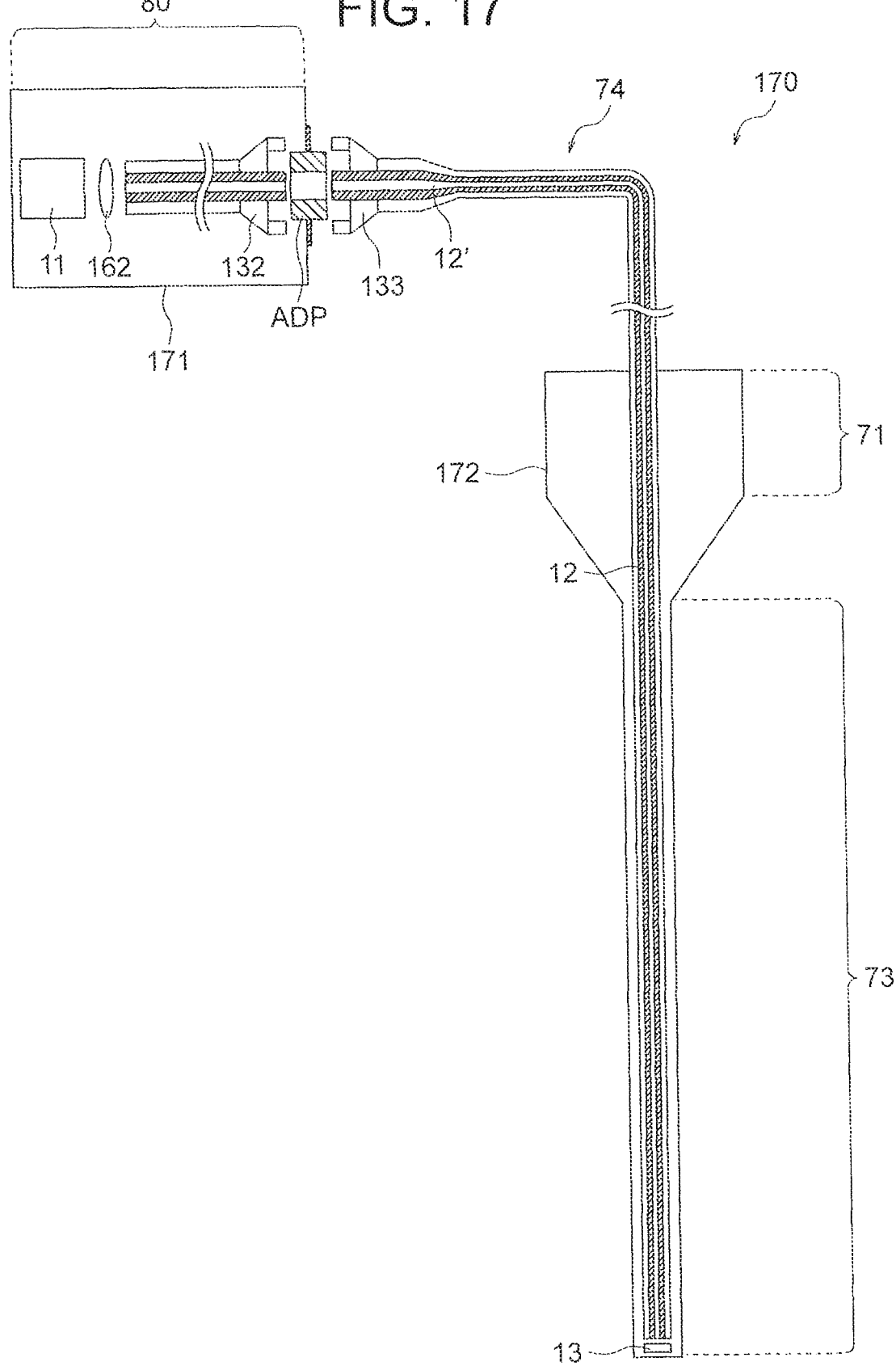
FIG. 17 is a diagram showing an optical apparatus of the present embodiment.

FIG. 17 is a diagram showing the optical apparatus of the present embodiment. Same reference numerals are assigned to components that are same as in FIG. 8 and components that are same as in FIG. 16, and description thereof is omitted.

An optical apparatus 170 is a non-wireless endoscope. The optical apparatus 170 includes a first housing 171 and a second housing 172. The first housing 171 includes the light source unit 80. The second housing 172 includes the holding portion 71, the first tubular portion 73, and the second tubular portion 74.

The light source 11, the lens 162, the optical connector 132, and the optical adapter ADP are disposed at an interior of the housing 171. The light guiding member 12 and the wavelength converting member 13 are disposed at an interior of the housing 172.

The first tubular portion 73 and the second tubular portion 74 are mainly constituted by the second light guiding area 12". The optical connector 133 is positioned at a front end of the second tubular portion 74. The first light guiding area 12' is located near the optical connector 133.

In the optical apparatus 170, the first tubular portion 73 and the second tubular portion 74 are mainly constituted by the second light guiding area 12". Therefore, it is possible to make the first tubular portion 73 and the second tubular portion 74 thin. As a result, it is possible to insert the first tubular portion 73 easily into a body or a metal tube. Moreover, handling of the second housing 172 becomes easy.

In the optical apparatus 170, the first housing 171 and the second housing 172 are connected by the pair of connectors. Accordingly, at the time of fabricating, it is possible to fabricate by separating apart the first housing and the second housing. Therefore, it is possible to increase a degree of freedom of fabricating. Moreover, repairing becomes easy.

An arrangement may be made such that the first housing can be used for a plurality of second housings. In this case, one second housing is to be chosen from housings of a plurality of types, and the second housing chosen is to be connected to the first housing. Even in a case in which the second housing is discarded after use, the first housing can be used repeatedly.

(Optical Apparatus 15 of Present Embodiment)

Figure 18:
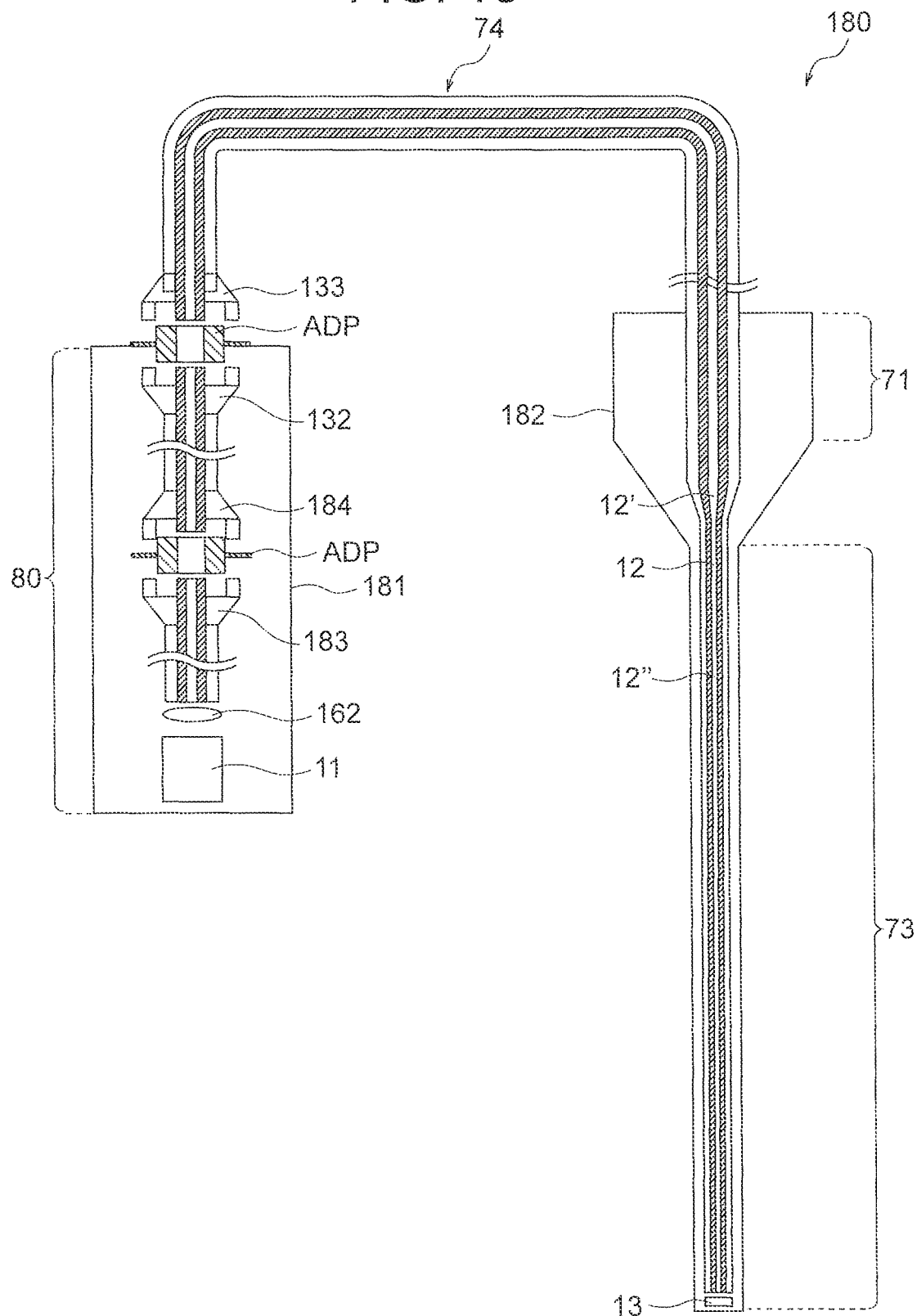
FIG. 18 is a diagram showing an optical apparatus of the present embodiment.

FIG. 18 is a diagram showing an optical apparatus of the present embodiment. Same reference numerals are assigned to components that are same as in FIG. 17, and description thereof is omitted.

An optical apparatus 180 is a non-wireless endoscope. The optical apparatus 180 includes a first housing 181 and a second housing 182. The first housing 181 includes the light source unit 80. The second housing 182 includes the holding portion 71, the first tubular portion 73, and the second tubular portion 74.

The light source 11, the lens 162, an optical connector 183, the optical adapter ADP, an optical connector 184, the optical connector 132, and the optical adapter ADP are disposed at an interior of the first housing 181. The light guiding member 12 and the wavelength converting member 13 are disposed at an interior of the second housing 182.

The first tubular portion 73 is mainly constituted by the second light guiding area 12". The optical connector 133 is positioned at a front end of the second tubular portion 74. The first light guiding area 12' is positioned at the interior of the second housing 182.

In the optical apparatus 180, the first tubular portion 73 is mainly constituted by the second light guiding area 12". Therefore, it is possible to make the first tubular portion 73 thin. As a result, it is possible to insert the first tubular portion 73 into a body or a metal tube.

An arrangement may be made such that the first tubular portion 73 and the second tubular portion 74 are mainly constituted by the second light guiding area 12" similarly as in the optical apparatus 170.

In the optical apparatus 180, the pair of optical connectors is disposed at the interior of the first housing 181. Accordingly, at the time of fabricating, it is possible to fabricate by separating apart the first housing and the second housing. Therefore, it is possible to increase a degree of freedom of fabricating. Moreover, repairing becomes easy.

(Optical Apparatus 16 of Present Embodiment)

It is preferable that an optical apparatus of the present embodiment include an optical converting unit, and the optical converting unit include a holding member, a reflecting member, and an optical converting member. Moreover, it is preferable that a recess be formed in the holding member, the reflecting member and the optical converting member be disposed in the recess, a diameter of one end surface of the recess be smaller than a diameter of the other end surface of the recess, and the one end surface of the recess be located on an exit end side.

The optical converting unit, being already described in the first example of the wavelength converting unit (wavelength converting unit 90), the second example of the wavelength converting unit (wavelength converting unit 100), and the light diffusing unit, description thereof is omitted.

Fine particles may have been included in the wavelength converting member. By the fine particles, it is possible to diffuse light. Moreover, a diffusing member may have been disposed separately apart from the wavelength converting member. For instance, in the wavelength converting unit 90, a diffusing member may be disposed adjacent to the wavelength converting member 93. Only the diffusing member may have been disposed.

Moreover, the wavelength converting members may have been disposed in plurality. For instance, in the wavelength converting unit 100, the wavelength converting member 93 is to be disposed adjacent to the wavelength converting member 103.

(Optical Apparatus 17 of Present Embodiment)

In an optical apparatus of the present embodiment, it is possible to dispose another light guiding member between the light source and the light guiding member.

Figure 19A:
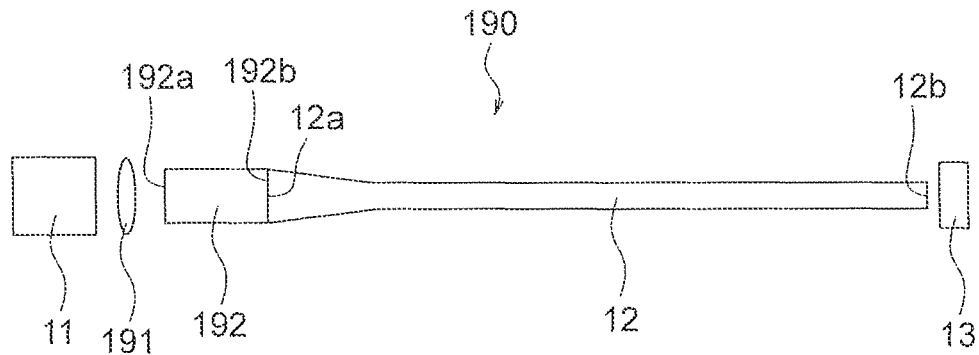
FIG. 19A, FIG. 19B, and FIG. 19C are diagrams showing the optical apparatus of the present embodiment.
Figure 19B:
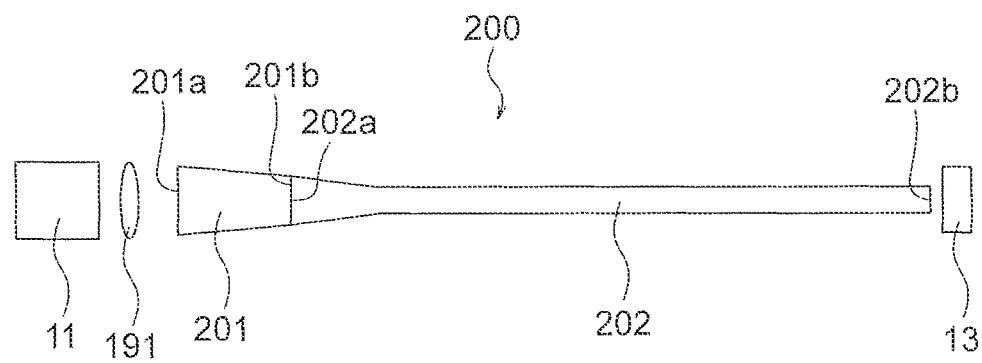
Figure 19C:
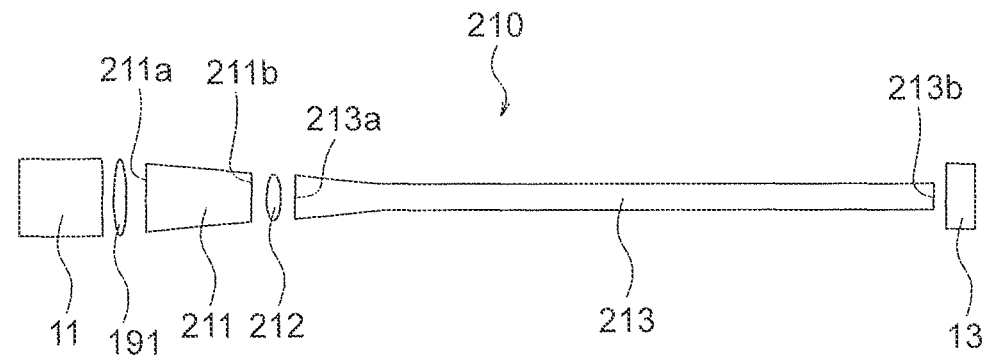

FIG. 19A, FIG. 19B, and FIG. 19C are diagrams showing an optical apparatus of the present embodiment. FIG. 19A is a diagram showing a third example of an internal configuration of the optical apparatus. FIG. 19B is a diagram showing a fourth example of the internal configuration. FIG. 9C is a diagram showing a fifth example of the internal configuration. Same reference numerals are assigned to components that are same as in FIG. 2A, and description thereof is omitted.

In the third example, as shown in FIG. 19A, an optical apparatus 190 includes the light source 11, a lens 191, a light guiding member 192, the light guiding member 12, and the wavelength converting member 13.

Light emitted from the light source 11 is focused by the lens 191. The light guiding member 192 is disposed at a focusing position. Accordingly, it is possible to make the light emanated from the light source 11 incident on the light guiding member 192.

Light incident on the light guiding member 192 emanates from the light guiding member 192. Light emanated from the light guiding member 192 is incident on the light guiding member 12.

The light guiding member 192 includes an incidence end surface 192a and an exit end surface 192b. A diameter of the incidence end surface 192a and a diameter of the exit end surface 192b are same. A diameter of the exit end surface 192b and a diameter of the incidence end surface 12a are same.

From the incidence end surface 192a up to the exit end surface 192b, the diameter of the incidence end surface 192a, the diameter of the exit end surface 192b, and the diameter of the incidence end surface 12a are the largest diameters.

In the optical apparatus 190, an end surface having the largest diameter is positioned on the light source 11 side. Therefore, it is possible to make the light emitted from the light source 11 incident efficiently on the light guiding member.

In the fourth example, as shown in FIG. 19B, an optical apparatus 200 includes the light source 11, the lens 191, a light guiding member 201, a light guiding member 202, and the wavelength converting member 13.

Light emitted from the light source 11 is focused by the lens 191. The light guiding member 201 is disposed at a focusing position. Accordingly, it is possible to make the light emitted from the light source 11 incident on the light guiding member 201.

Light incident on the light guiding member 201 emanates from the light guiding member 201. Light emanated from the light guiding member 201 is incident on the light guiding member 202.

The light guiding member 201 has an incidence end surface 201a and an exit end surface 201b. The light guiding member 202 has an incidence end surface 202a and an exit end surface 202b.

A diameter of the incidence end surface 201a is larger than a diameter of the exit end surface 201b. A diameter of the incidence end surface 202a is larger than a diameter of the exit end surface 202b. The diameter of the exit end surface 201b and the diameter of the exit end surface 202a are same.

From the incidence end surface 201a up to the exit end surface 202b, the diameter of the incidence end surface 201a is the largest diameter.

In the optical apparatus 200, an end surface having the largest diameter is positioned on the light source 11 side. Therefore, it is possible to make the light emitted from the light source 11 incident on the light guiding member.

In the fifth example, as shown in FIG. 19C, an optical apparatus 210 includes the light source 22, the lens 191, a light guiding member 211, a lens 212, a light guiding member 213, and the wavelength converting member 13.

Light emitted from the light source 11 is focused by the lens 191. The light guiding member 211 is disposed at a focusing position. Accordingly, it is possible to make the light emitted from the light source 11 incident on the light guiding member 211.

Light incident on the light guiding member 211 emanates from the light guiding member 211. Light emanated from the light guiding member 211 is focused by the lens 212. The light guiding member 213 is disposed at a focusing position. Accordingly, it is possible to make the light emanated from the light guiding member 211 incident on the light guiding member 213.

The light guiding member 211 has an incidence end surface 211a and an exit end surface 211b. The light guiding member 213 has an incidence end surface 213a and an exit end surface 213b.

A diameter of the incidence end surface 211a is larger than a diameter of the exit end surface 211b. A diameter of the incidence end surface 213a is larger than a diameter of the exit end surface 213b. The diameter of the exit end surface 211b is larger than the diameter of the incidence end surface 213a.

From the exit end surface 211a up to the exit end surface 213b, the diameter of the incidence end surface 211a is the largest diameter.

In the optical apparatus 210, the end surface having the largest diameter is positioned on the light source 11 side. Therefore, it is possible to make the light emitted from the light source 11 incident efficiently on the light guiding member.

In the optical apparatus of the present embodiment, it is preferable that the light guiding member be a tapered optical fiber of which a diameter becomes thinner gradually from the incidence end surface toward the exit end surface.

(Optical Apparatus 17 of Present Embodiment)

A wireless endoscope of the present embodiment includes a long and slender insertion portion which is flexible, an operating portion which is provided to a rear end of the insertion portion. The insertion portion has a front-end portion which is provided to a front end of the insertion portion, a bending portion which is provided to a rear end of the front-end portion, and a flexible tubular portion which is extended from a rear end of the bending portion up to a front end of the operating portion. A light source is disposed on an operating portion side of the rear end of the insertion portion, an optical converting member is disposed at the front-end portion, a light guiding member formed of a medium having a refractive index higher than 1 is disposed between the light source and the optical converting member. Light emitted from the light source is incident on an incident end surface of the light guiding member, light emanated from an exit end surface of the light guiding member is irradiated to the optical converting member. The light guiding member has a first light guiding area having an incidence end surface and a second light guiding area having an exit end surface, a diameter of the incidence end surface is larger than a diameter of the exit end surface, a length of the first light guiding area is shorter than a length of the second light guiding area, and at least a part of the second light guiding area is included in the insertion portion.

Figure 20:
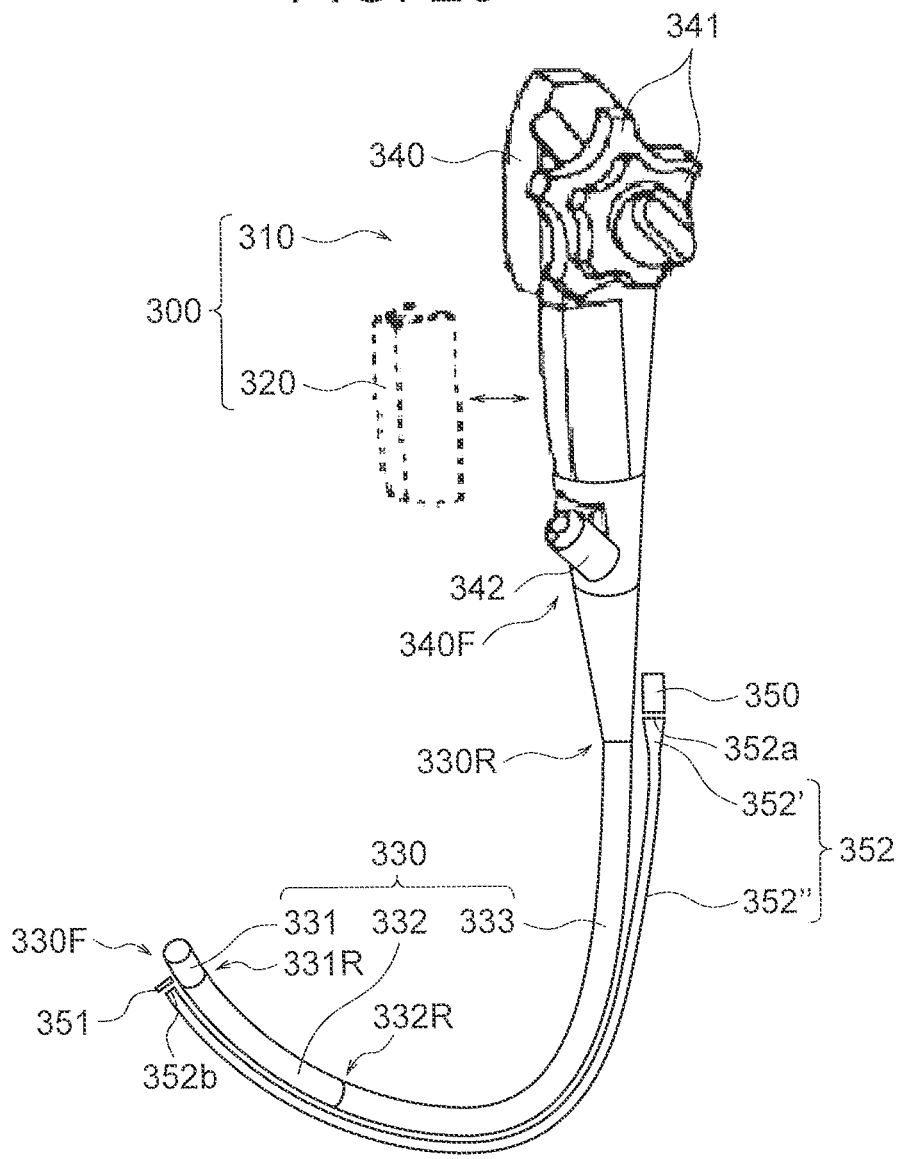
FIG. 20 is a diagram showing a wireless endoscope.

FIG. 20 is a diagram showing a wireless endoscope. A wireless endoscope 300 includes a wireless endoscope main body 310 (hereinafter, referred to as 'main body 310') and a battery 320. The battery 320 is detachably mounted on (connected to) the main body 310.

The main body 310 includes an insertion portion 330 and an operating portion 340. The insertion portion 330 is long and slender, and has flexibility. The operating portion 340 is provided to a rear end (base end) 330R of the insertion portion.

The insertion portion 330 includes a front-end portion 331, bending portion 332, and a flexible tubular portion 333. The front-end portion 331 is provided to a front end 330F of the insertion portion. The bending portion 332 is provided to a rear end 331R of the front-end portion. The flexible tubular portion 333 is extended from a rear end 332R of the bending portion up to a front end 340F of the operating portion.

The operating portion 340 is provided with a bending operation knob 341. By the bending operation knob 341, it is possible to bend the bending portion 332 in a vertical direction and a leftward-rightward direction. Moreover, a treatment tool insertion opening 342 is provided near the front end 340F of the operating portion. It is possible to insert the treatment tool from the treatment-tool insertion opening 342.

A light source 350 is disposed on an operating portion 340 side of the rear end 330R of the insertion portion. An optical converting member 351 is disposed at the front-end portion 331. A light guiding member 352 is disposed between the light source 350 and the optical converting member 351. The light guiding member 352 is formed of a medium having a refractive index higher than 1.

Light emitted from the light source 350 is incident on an incidence end surface of the light guiding member 352. Light emanated from an exit end surface of the light guiding member 352 is irradiated to the optical converting member 351.

The light guiding member 352 has a first light guiding area 352' and a second light guiding area 352". The first light guiding area 352' has an incidence end surface 352a. The second light guiding area 352" has an exit end surface 352b.

A diameter of the incidence end surface 352a is larger than a diameter of the exit end surface 352b. A diameter of the second light guiding area 352" is equal to a diameter of the exit end surface 352b. A length of the first light guiding area 352' is shorter than a length of the second light guiding area 352".

In the wireless endoscope 300, the insertion portion 330 is mainly constituted by the second light guiding area 352". The diameter of the second light guiding area 352" is extremely small. Therefore, in the wireless endoscope 300, it is possible to make a thickness of the insertion portion 330 thin. At least a part of the insertion portion 330 is inserted into a body or a metal tube for example. Accordingly, it is possible to insert the insertion portion 330 easily.

Moreover, the first light guiding area 352' is located between the light source 350 and the second light guiding area 352". Therefore, it is possible to make light emitted from the light source 350 incident efficiently on the first light guiding area 352'.

Furthermore, it is possible to make light incident on the first light guiding area 352' travel efficiently from the first light guiding area 352' to the second light guiding area 352". In this case, since it is possible to irradiate bright light to the optical converting member 351, it is possible to achieve bright illumination light.

(Endoscope System of Present Embodiment)

An endoscope system of the present embodiment includes the optical apparatus of the present embodiment or the wireless endoscope of the present embodiment, and a processing apparatus.

As described in the first example of the optical system (FIG. 1A), the optical system 1 includes an image sensor. Moreover, as described in the second example of the optical system (FIG. 1B), the image pickup apparatus is to be connected to the optical apparatus 4. Accordingly, in the optical apparatus 1, it is possible to output image data acquired by the image sensor by the wireless transmission. In the optical apparatus 4, it is possible to output image data acquired by the image pickup apparatus by the wired transmission.

Therefore, a processing apparatus capable of receiving image data is to be provided separately apart from the optical apparatus. By making such arrangement, it is possible to acquire image data.

In a case in which the optical apparatus of the present embodiment is an endoscope, it is possible to build an endoscope system by combining various apparatuses such as a processing unit with the optical apparatus of the present embodiment.

According to the present disclosure, it is possible to provide an endoscope and an endoscope system in which the thickness of the tubular portion is thin and in which illumination light can be incident efficiently on the light guiding member disposed inside the tubular portion.

The present disclosure is suitable for an endoscope and an endoscope system in which the thickness of the tubular portion is thin and in which illumination light can be incident efficiently on the light guiding member disposed inside the tubular portion.

What is claimed is:

1. An endoscope comprising:
an insertion portion which is long and slender;
an intermediate portion which is provided to a base-end side of the insertion portion;
an operating portion which is provided to a holding portion, the holding portion being provided to a base-end side of the intermediate portion;
an optical converting member which is provided to the insertion portion;
a light source which is provided to the holding portion; and
a light guide which is inserted through the insertion portion,
wherein the light guide has a first light guiding area which is provided on the operating portion side, and which has an incidence end surface on which light from the light source is incident, and a second light guiding area having an exit end surface from which the light emanates,
a diameter of the light guide of the first light guiding area becomes smaller toward the second light guiding area, and
the first light guiding area is provided to the intermediate portion;
light emitted from the light source is incident on the incidence end surface of the light guide, and is irradiated to the optical converting member from the exit end surface of the light guide; and
the following conditional expression is satisfied:

$$LEF1 < \Delta EF$$

where,
LEF1 denotes an optical coupling efficiency of the light guide, and is expressed by LEF1=Iout/Iin,
$\Delta EF$ denotes a difference in a conversion efficiency of the optical converting member, and is expressed by $\Delta EF=|EFa-EFb|$,
Iout denotes an intensity of light incident on the incidence end surface,
Iin denotes an intensity of light emanating from the exit end surface,
EFa denotes a conversion efficiency when a diameter of the exit end surface is φa,
EFb denotes a conversion efficiency when the diameter of the exit end surface is φb,
the conversion efficiency is expressed by Q/P,
P denotes an intensity of light irradiated to the optical converting member,
Q denotes an intensity of light radiated from the optical converting member,
φa denotes a diameter of the incidence end surface, and
φb denotes a diameter of the exit end surface.

2. The endoscope according to claim 1, wherein the light guide of the first light guiding area has a tapered shape which becomes thinner toward the second light guiding area.

3. The endoscope according to claim 1, wherein
the second light guiding area is provided throughout the entire insertion portion, and
a diameter of the light guide of the second light guiding area is constant up to the exit end surface.

4. The endoscope according to claim 1, comprising:
a first housing; and
a second housing, wherein
the light source is disposed inside the first housing,
the light guide and the optical converting member are disposed inside the second housing, and
the first housing and the second housing are mutually independent.

5. The endoscope according to claim 1, wherein
the optical converting member is the wavelength converting member, and
following conditional expression is satisfied $$(\phi a / \phi b)^2 \times (NAa/NAb)^2 < 1/2 + (1/2) \times \{(\phi b/(2 \times d'))^2 + 1\}^{-1/2}$$

where,
NAa denotes a numerical aperture of the incidence end surface,
NAb denotes a numerical aperture of the exit end surface, and
d' denotes a distance from the exit end surface up to the optical converting member.

6. The endoscope according to claim 1, wherein
an optical coupler is disposed between the light source and the light guide,
the optical coupler has a core and a clad, and
a diameter of the core is same as the diameter of the incidence end surface.

7. The endoscope according to claim 6, wherein
the optical converting member is the wavelength converting member,
light of a first wavelength band is emitted from the light source,
in the wavelength converting member, light of a second wavelength band is generated from the light of the first wavelength band,
light of a wavelength longer than the first wavelength band is included in the light of the second wavelength band, and
following conditional expression is satisfied:

$$LEF1cou < \Delta EF'$$

where,
LEF1cou=LEF1+ΔLEFcou,
LEF1 denotes an optical coupling efficiency of the light guide, and is expressed by LEF1=Iout/Iin,
ΔLEFcou denotes a difference in an optical coupling efficiency of the optical coupler, and is expressed by ΔLEFcou=|LEFcoua−LEFcoub|
Iout denotes an intensity of light incident on the incidence end surface,
Iin denotes an intensity of light emanating from the exit end surface,
LEFcoua denotes an optical coupling efficiency when a diameter of the core is ϕa,
LEFcoub denotes an optical coupling efficiency when the diameter of the core is ϕb,
ΔEF' denotes a difference in conversion efficiency of the optical converting member, and is expressed by ΔEF'=|EFa'−EFb'|,
EFa' denotes a conversion efficiency when a diameter of the exit end surface is ϕa,
EFb' denotes a conversion efficiency when a diameter of the exit end surface is ϕb,
the conversion efficiency is expressed by Q'/P',
P' denotes an intensity of light of the first wavelength band irradiated to the wavelength converting member, and
Q' denotes one of an intensity of light of the second wavelength band, and a sum of the intensity of the light of the second wavelength band and an intensity of light of the first wavelength band that has transmitted through the wavelength converting member.

8. The endoscope according to claim 1, wherein
the light guide comprises a first light guide;
a pair of optical connectors is disposed between the light source and the first light guide,
the optical connector includes a second light guide and a holding member, and
a diameter of the second light guide of the optical connector is same as the diameter of the incidence end surface.

9. The endoscope according to claim 8, wherein
the optical converting member is the wavelength converting member,
light of a first wavelength band is emitted from the light source,
in the wavelength converting member, light of second wavelength band is generated from the light of the first wavelength band,
light of a wavelength longer than the first wavelength band is included in the light of the second wavelength band, and
following conditional expression is satisfied:

$$LEF1cne < \Delta EF'$$

where,
LEF1cne=LEF1+ΔLEFcne,
LEF1 denotes an optical coupling efficiency of the first light guide, and is expressed by LEF1=Iout/Iin,
ΔLEFcne denotes a difference in an optical coupling efficiency of the optical connector, and is expressed by ΔLEFcne=|LEFcnea−LEFcneb|
Iout denotes an intensity of light incident on the incidence end surface,
Iin denotes an intensity of light emanating from the exit end surface,
LEFcnea denotes an optical coupling efficiency when a diameter of the second light guide of the optical connector is ϕa,
LEFcneb denotes an optical coupling efficiency when a diameter of the second light guide of the optical connector is ϕb,
ΔEF' denotes a difference in conversion efficiency of the wavelength converting member, and is expressed by ΔEF'=|EFa'-EFb'|,
EFa' denotes a conversion efficiency when a diameter of the exit end surface is ϕa, EFb' denotes a conversion efficiency when the diameter of the exit end surface is φb,
the conversion efficiency is expressed by Q'/P',
P' denotes an intensity of the light of the first wavelength band irradiated to the wavelength converting member, and
Q' denotes one of an intensity of light of the second wavelength band, and a sum of the intensity of the light of the second wavelength band and an intensity of light of the first wavelength band that has transmitted through the wavelength converting member.

10. The endoscope according to claim 8, comprising:
a housing which has the holding portion and the tubular portion, wherein
the light source, the pair of optical connectors, the first light guide, and the optical converting member are disposed in the housing.

11. The endoscope according to claim 8, comprising:
a first housing; and
a second housing, wherein
the first housing includes the one optical connector, and
the second housing includes the other optical connector.

12. An endoscope comprising:
an insertion portion which is long and slender;
an intermediate portion which is provided to a base-end side of the insertion portion;
an operating portion which is provided to a holding portion, the holding portion being provided to a base-end side of the intermediate portion;
an optical converting member which is provided to the insertion portion;
a light source which is provided to the holding portion; and
a light guide which is inserted through the insertion portion,
wherein the light guide has a first light guiding area which is provided on the operating portion side, and which has an incidence end surface on which light from the light source is incident, and a second light guiding area having an exit end surface from which the light emanates,
a diameter of the light guide of the first light guiding area becomes smaller toward the second light guiding area,
the first light guiding area is provided to the intermediate portion;
light emitted from the light source is incident on the incidence end surface of the light guide, and is irradiated to the optical converting member from the exit end surface of the light guide; and
the following conditional expression is satisfied $$(\phi a/\phi b)^2 \times (NAa/NAb)^2 < 1/2 + (1/2) \times \{(\phi b/(2 \times d))^2 + 1\}^{-1/2}$$

where,
φa denotes a diameter of the incidence end surface,
φb denotes a diameter of the exit end surface,
NAa denotes a numerical aperture of the incidence end surface,
NAb denotes a numerical aperture of the exit end surface, and
d denotes a distance from the exit end surface up to the optical converting member.

13. An endoscope comprising:
an insertion portion which is long and slender;
an intermediate portion which is provided to a base-end side of the insertion portion;
an operating portion which is provided to a holding portion, the holding portion being provided to a base-end side of the intermediate portion;
an optical converting member which is provided to the insertion portion;
a light source which is provided to the holding portion; and
a light guide which is inserted through the insertion portion,
wherein the light guide has a first light guiding area which is provided on the operating portion side, and which has an incidence end surface on which light from the light source is incident, and a second light guiding area having an exit end surface from which the light emanates,
a diameter of the light guide of the first light guiding area becomes smaller toward the second light guiding area,
the first light guiding area is provided to the intermediate portion;
light emitted from the light source is incident on the incidence end surface of the light guide, and is irradiated to the optical converting member from the exit end surface of the light guide;
an optical coupler is disposed between the light source and the light guide,
the optical coupler has a core and a clad, and
a diameter of the core is same as the diameter of the incidence end surface; and
the following conditional expression is satisfied:

$$LEF1cou < \Delta EF$$

where,
LEF1cou=LEF1+ΔLEFcou,
LEF1 denotes an optical coupling efficiency of the light guide, and is expressed by LEF1=Iout/Iin,
ΔLEFcou denotes a difference in an optical coupling efficiency of the optical coupler, and is expressed by ΔLEFcou=|LEFcoua−LEFcoub|,
Iout denotes an intensity of light incident on the incidence end surface,
Iin denotes an intensity of light emanating from the exit end surface,
LEFcoua denotes an optical coupling efficiency when a diameter of the core is φa,
LEFcoub denotes an optical coupling efficiency when a diameter of the core is φb,
ΔEF denotes a difference in the conversion efficiency of the optical converting member, and is expressed by ΔEF=|EFa−EFb|,
EFa denotes a conversion efficiency when the diameter of the exit end surface is φa,
EFb denotes a conversion efficiency when the diameter of the exit end surface is φb,
the conversion efficiency is expressed by Q/P,
P denotes an intensity of light irradiated to the optical converting member,
Q denotes an intensity of light radiated from the optical converting member,
φa denotes a diameter of the incidence end surface, and
φb denotes a diameter of the exit end surface.

14. An endoscope comprising:
an insertion portion which is long and slender;
an intermediate portion which is provided to a base-end side of the insertion portion;
an operating portion which is provided to a holding portion, the holding portion being provided to a base-end side of the intermediate portion;
an optical converting member which is provided to the insertion portion;
a light source which is provided to the holding portion; and
a light guide which is inserted through the insertion portion,
wherein the light guide has a first light guiding area which is provided on the operating portion side, and which has an incidence end surface on which light from the light source is incident, and a second light guiding area having an exit end surface from which the light emanates,
a diameter of the light guide of the first light guiding area becomes smaller toward the second light guiding area,
the first light guiding area is provided to the intermediate portion;
light emitted from the light source is incident on the incidence end surface of the light guide, and is irradiated to the optical converting member from the exit end surface of the light guide; and
the following conditional expression is satisfied:

$$LEF1cne < \Delta EF$$

where,
$LEF1cne = LEF1 + \Delta LEFcne$,
LEF1 denotes an optical coupling efficiency of the first light guide, and is expressed by $LEF1 = Iout/Iin$,
$\Delta LEFcne$ denotes a difference in an optical coupling efficiency of the optical connector, and is expressed by $\Delta LEFcne = |LEFcnea - LEFcneb|$
Iout denotes an intensity of light incident on the incidence end surface,
Iin denotes an intensity of light emanating from the exit end surface,
LEFcnea denotes an optical coupling efficiency when a diameter of the second light guide of the optical connector is $\phi a$,
LEFcneb denotes an optical coupling efficiency when a diameter of the second light guide of the optical connector is $\phi b$,
$\Delta EF$ denotes a difference in conversion efficiency of the optical converting member, and is expressed by $\Delta EF = |EFa - EFb|$,
EFa denotes a conversion efficiency when a diameter of the exit end surface is $\phi a$,
EFb denotes a conversion efficiency when a diameter of the exit end surface is $\phi b$,
the conversion efficiency is expressed by Q/P,
P denotes an intensity of light irradiated to the optical converting member,
Q denotes an intensity of light radiated from the optical converting member,
$\phi a$ denotes a diameter of the incidence end surface, and
$\phi b$ denotes a diameter of the exit end surface.

* * * * *